US009671386B2

(12) United States Patent
Flinn et al.

(10) Patent No.: US 9,671,386 B2
(45) Date of Patent: Jun. 6, 2017

(54) DETECTION OF THERMAL DAMAGE OF COMPOSITES USING MOLECULAR PROBES

(71) Applicant: University of Washington through its Center for Commercialization, Seattle, WA (US)

(72) Inventors: Brian D. Flinn, Seattle, WA (US); Alex Kwan-yue Jen, Kenmore, WA (US); Sei-Hum Jang, Seattle, WA (US); Tucker Howie, Seattle, WA (US); Zhengwei Shi, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 429 days.

(21) Appl. No.: 14/267,718

(22) Filed: May 1, 2014

(65) Prior Publication Data

US 2014/0328369 A1     Nov. 6, 2014

Related U.S. Application Data

(60) Provisional application No. 61/916,063, filed on Dec. 13, 2013, provisional application No. 61/818,315, filed on May 1, 2013.

(51) Int. Cl.
*G01N 33/44* (2006.01)
*G01K 11/20* (2006.01)
*G01N 21/64* (2006.01)

(52) U.S. Cl.
CPC .......... *G01N 33/442* (2013.01); *G01K 11/20* (2013.01); *G01N 21/643* (2013.01)

(58) Field of Classification Search
CPC .................................... G01K 11/20
(Continued)

(56) References Cited

U.S. PATENT DOCUMENTS 5,483,338 A    1/1996  Wachter
5,656,815 A *  8/1997  Justus ............... G01T 1/11
                                         250/337
(Continued)

FOREIGN PATENT DOCUMENTS

DE        3901988 A1 *  2/1990  ........... C07D 471/06

OTHER PUBLICATIONS

Howie et al ("Detection of Thermal Damage of CFRP Using Fluorescent Thermal Damage Probes," SAMPE Technical Conference, Charleston, SC (Oct. 22-25, 2012)).*

(Continued)

*Primary Examiner* — Minh Phan
*Assistant Examiner* — Leon W Rhodes, Jr.
(74) *Attorney, Agent, or Firm* — Christensen O'Connor Johnson Kindness PLLC

(57) ABSTRACT

Improved methods of detecting thermal exposure are provided herein. The provided methods utilize initially dormant luminescent probes incorporated into a matrix to form a composite. When exposed to heat over a period of time, the luminescent probes are "activated" through a molecular transformation initiated by thermal energy. The activated probes exhibit a luminescent profile based on the extent of thermal exposure, thereby providing an indicator of the thermal exposure experienced by the matrix. When the composite is used to produce a structural component of a vehicle (e.g., an aircraft), the methods provide a convenient, large-area indicator of thermal damage experienced by the structural component.

18 Claims, 15 Drawing Sheets

(58) Field of Classification Search
USPC .......................................................... 374/106
See application file for complete search history.

(56) References Cited

U.S. PATENT DOCUMENTS

| | | | |
|---|---|---|---|
| 6,756,120 B2 | 6/2004 | Smith | |
| 6,787,108 B2 | 9/2004 | Ribi | |
| 7,115,869 B2 | 10/2006 | Shelley | |
| 7,514,262 B2 | 4/2009 | Ribi | |
| 7,597,844 B2 | 10/2009 | Ribi | |
| 7,785,505 B2 | 8/2010 | Papazoglou | |
| 8,142,072 B2 | 3/2012 | Kinami | |
| 8,278,631 B2 | 10/2012 | Patel | |
| 8,529,682 B2 | 9/2013 | Prusik | |
| 8,569,208 B1 | 10/2013 | Ribi | |
| 8,617,900 B2 | 12/2013 | Ribi | |
| 9,372,177 B2* | 6/2016 | Georgeson | G01N 31/229 |
| 2007/0158624 A1 | 7/2007 | Weder | |
| 2010/0043695 A1 | 2/2010 | Reichert | |
| 2014/0328369 A1* | 11/2014 | Flinn | G01N 33/442 374/57 |

OTHER PUBLICATIONS

Anzenbacher, P., Jr., et al., "Hydrophilic Polymer Matrices in Optical Array Sensing," Current Opinion in Chemical Biology 14(6):693-704, Dec. 2010.

Dara, I.H., et al., "Heat-Damage Assessment of Carbon-Fiber-Reinforced Polymer Composites by Diffuse Reflectance Infrared Spectroscopy," Journal of Applied Polymer Science 96(4):1222-1230, May 2005.

Demchenko, A.P., "The Concept of λ-Ratiometry in Fluorescence Sensing and Imaging," Journal of Fluorescence 20(5):1099-1128, Sep. 2010.

Farquaharson, S., et al., "Measurement of Thermal Degradation in Epoxy Composites by FT-Raman Spectroscopy," Proceedings of the International Society for Optical Engineering (SPIE) 2072:319-331, Feb. 1994.

Fisher, W.G., et al., "Nondestructive Inspection of Graphite-Epoxy Composites for Heat Damage Using Laser-Induced Fluorescence," Applied Spectroscopy 49(9):1225-1231, Sep. 1995.

Howie, T., et al., "Thermal Damage Detection of CFRP Using Coatings Doped With Fluorescent Probes," Proceedings of SAMPE 2013, Education & Green Sky—Materials Technology for a Better World, Long Beach, Calif., May 6-9, 2013, 11 pages.

Hu, J., and S. Liu, "Responsive Polymers for Detection and Sensing Applications: Current Status and Future Developments," Macromolecules 43(20):8315-8330, Oct. 2010.

"Hypertac: Hyperboloid Contact Technology," © 2011 Hypertronics Corporation, Hudson, Mass., <http://hypertronics.com/en/Default.aspx> [retrieved Oct. 31, 2014], 1 page.

Lin, K.-F., and F.W. Wang, "Fluorescence Monitoring of Polarity Change and Gelation During Epoxy Cure," Polymer 35(4):687-691, Feb. 1994.

Pucci, A., et al., "Polymer Composites With Smart Optical Properties," Soft Matter 7(8):3689-3700, Apr. 2011.

Sathish, S., et al., "Thermo-Elastic Characterization of Heat Damage in Carbon Fiber Epoxy Composites," in D.O. Thompson and D.E. Chimenti (eds.), "AIP Conference Proceedings (CP820): Review of Quantitative Nondestructive Evaluation," Jul. 31-Aug. 5, 2005, Brunswick, Maine, American Institute of Physics, Melville, N.Y., vol. 25, pp. 1015-1018, Mar. 2006.

Street, K.N., et al., "Thermal Damage Effects on Delamination Toughness of a Graphite/Epoxy Composite," Composites Science and Technology 32(1):1-14, 1988.

Tandon, G.P., and K.V. Pochiraju, "Heterogeneous Thermo-Oxidative Behavior of Multidirectional Laminated Composites," Journal of Composite Materials 45(4):415-435, Feb. 2011.

Toivola, R.E., et al., "Damage Detection for Aerospace Composites Using Matrix Resins Functionalized With Fluorescent Probe Molecules," Proceedings of SAMPE 2013, Education & Green Sky—Materials Technology for a Better World, Long Beach, Calif., May 6-9, 2013, 15 pages.

Flinn, B.D., "Detection of Thermal Damage of Composites Using Molecular Probes," U.S. Appl. No. 61/916,063, filed Dec. 13, 2013.

Flinn, B.D., "Detection of Thermal Damage of Composites Using Molecular Probes," U.S. Appl. No. 61/818,315, filed May 1, 2013.

Allen, N.S., et al., "Phosphorescence From Epoxy Resins: Evidence for an Associated Ground-State Aggregate and Triplet Excimer," Polymer Photochemistry 2(5):389-393, Sep. 1982.

Allen, N.S., et al., "Spectroscopic Properties and Photosensitivity of Epoxy Resins," Polymer Photochemistry 2(2):97-107, Mar. 1982.

Anderson, B.J., "Thermal Stability of High Temperature Epoxy Adhesives by Thermogravimetric and Adhesive Strength Measurements," Polymer Degradation and Stability 96(10):1874-1881, Oct. 2011.

Azizian, F., et al., "Reductive Alkylation of Aminofluorans: A Simple Route to Intrinsically Thermochromic Fluorans," Dyes and Pigments 99(2):432-439, Nov. 2013.

Bamfield, P., and M.G. Hutchings, "1.9.1 Piezochromism," in "Chromic Phenomena: Technological Applications of Colour Chemistry," RSC Publishing, Cambridge, U.K., pp. 104-105, Feb. 2010.

Barilero, T., et al., "Fluorescent Thermometers for Dual-Emission-Wavelength Measurements: Molecular Engineering and Application to Thermal Imaging in a Microsystem," Analytical Chemistry 81(19):7988-8000, Aug. 2009.

Beckham, H.W., and M.F. Rubner, "Synthesis and Optical Properties of a New Class of Polyamides Containing Reactive Diacetylene Groups," Macromolecules 22(5):2130-2138, May 1989.

Bellenger, V., and J. Verdu, "Photooxidation of Amine Crosslinked Epoxies: II. Influence of Structure," Journal of Applied Polymer Science 28(9):2677-2688, Sep. 1983.

Beyer, M.K., and H. Clausen-Schaumann, "Mechanochemistry: The Mechanical Activation of Covalent Bonds," Chemical Reviews 105(8):2921-2948, Jul. 2005.

Bowles, K.J., "Durability of Graphite-Fiber-Reinforced PMR-15 Composites Aged at Elevated Temperatures," Journal of Composites, Technology and Research 21(3):127-132, Jul. 1999.

Bowles, K.J., et al., "The Effects of Fiber Surface Modification and Thermal Aging on Composite Toughness and Its Measurement," Journal of Composite Materials 31(6):552-579, Mar. 1997.

Bowles, K.J., et al., "Thermal-Stability Relationships Between PMR-15 Resin and Its Composites," Journal of Advanced Materials 26(1):23-32, Oct. 1994.

Brady, S.K., et al., "NMR Detection of Thermal Damage in Carbon Fiber Reinforced Epoxy Resins," Journal of Magnetic Resonance 172(2):342-345, Feb. 2005.

Buch, X., and M.E.R. Shanahan, "Influence of the Gaseous Environment on the Thermal Degradation of a Structural Epoxy Adhesive," Journal of Applied Polymer Science 76(7):987-992, May 2000.

Buch, X., and M.E.R. Shanahan, "Migration of Cross-Linking Agents to the Surface During Ageing of a Structural Epoxy Adhesive," International Journal of Adhesion and Adhesives 23(4):261-267, 2003.

Buch, X., and M.E.R. Shanahan, "Thermal and Thermo-Oxidative Ageing of an Epoxy Adhesive," Polymer Degradation and Stability 68(3):403-411, May 2000.

Bur, A.J., et al., "Fluorescence Based Temperature Measurements and Applications to Real-Time Polymer Processing," Polymer Engineering & Science 41(8):1380-1389, Aug. 2001.

Calado, V.M.A., and S.G. Advani, "2. Thermoset Resin Cure Kinetics and Rheology," in Davé and Loos (eds.), "Processing of Composites," Hanser Verlag GmbH, Cincinatti, Ohio, 2000, pp. 32-107.

Cantwell, W.J., et al., "An Assessment of the Impact Performance of CFRP Reinforced With High-Strain Carbon Fibres," Composites Science and Technology 25(2):133-148, 1986.

Carpick, R.W., et al., "Spectroscopic Ellipsometry and Fluorescence Study of Thermochromism in an Ultrathin Poly(diacetylene) Film: Reversibility and Transition Kinetics," Langmuir 16(10):4639-4647, Apr. 2000.

(56) References Cited

OTHER PUBLICATIONS

Chandrasekharan, N., and L.A. Kelly, "A Dual Fluorescence Temperature Sensor Based on Perylene/Exciplex Interconversion," Journal of the American Chemical Society 123(40):9898-9899, Sep. 2001.
Charier, S., et al., "An Efficient Fluorescent Probe for Ratiometric pH Measurements in Aqueous Solutions," Angewandte Chemie International Edition 43(36):4785-4788, Sep. 2004.
Charier, S., et al., "Photophysics of a Series of Efficient Fluorescent pH Probes for Dual-Emission-Wavelength Measurements in Aqueous Solutions," Chemistry—A European Journal 12(4):1097-1113, Jan. 2006.
Crenshaw, B.R., and C. Weder, "Deformation-Induced Color Changes in Melt-Processed Photoluminescent Polymer Blends," Chemistry of Materials 15(25):4717-4724, Nov. 2003.
Crenshaw, B.R., et al., "Deformation-Induced Color Changes in Mechanochromic Polyethylene Blends," Macromolecules 40(7):2400-2408, Mar. 2007.
Crenshaw, B.R., et al., "Threshold Temperature Sensors With Tunable Properties," Macromolecular Chemistry and Physics 208(6):572-580, Mar. 2007.
Creton, R., "The Calcium Pump of the Endoplasmic Reticulum Plays a Role in Midline Signaling During Early Zebrafish Development," Developmental Brain Research 151(1-2):33-41, Jul. 2004.
Damian, C., et al., "Influence of Three Ageing Types (Thermal Oxidation, Radiochemical and Hydrolytic Ageing) on the Structure and Gas Transport Properties of Epoxy—Amine Networks," Polymer Degradation and Stability 72(3):447-458, Jun. 2001.
Dara, I.H., et al., "Heat-Damage Assesment of Carbon-Fiber-Reinforced Polymer Composites by Diffuse Reflectance Infrared Spectroscopy." Journal of Applied Polymer Science 96(4):1222-1230, May 2005.
Davis, D.A., et al., "Force-Induced Activation of Covalent Bonds in Mechanoresponsive Polymeric Materials," Nature 459(7243):68-72, May 2009.
Demchenko, A.P., "The Concept of λ-Ratiometry in Fluorescence Imaging," Journal of Fluorescence 20(5):1099-1128, Sep. 2010.
"Designation: F1416-96 (Reapproved 2003): Standard Guide for Selection of Time-Temperature Indicators," ASTM International, accessed Nov. 2016, 4 pages.
Donald, A.M., "Crazing," in Haward and Young (eds.), "The Physics of Glassy Polymers," 2nd ed., New York, 1997, Chap. 6, pp. 295-341.
Drickamer, H.G., et al., "Two Examples of Pressure Tuning Spectroscopy in Solid Polymeric Media," Industrial & Engineering Chemistry Research 40(14):3038-3041, Apr. 2001.
Farquharson, S., et al., "Measurement of Thermal Degradation in Epoxy Composites by FT-Raman Spectroscopy," Proceedings of SPIE 2072:319-331, Feb. 1994.
Fisher, W.G., et al., "Laser Induced Fluorescence Imaging of Thermal Damage in Polymer Matrix Composites," Materials Evaluation 55(6):726-729, Jun. 1997.
Fisher, W.G., et al., "Nondestructive Inspection of Graphite-Epoxy Composites Heat Damage Using Laser-Induced Fluorescence," Applied Spectroscopy 49(9):1225-1231, Sep. 1995.
Galagan, Y., and W.-F. Su, "Fadable Ink for Time-Temperature Control of Food Freshness: Novel New Time-Temperature Indicator," Food Research International 41(6):653-657, Jul. 2008.
Gentili, D., et al., "A Time-Temperature Integrator Based on Fluorescent and Polymorphic Compounds," Scientific Reports 3:258, Sep. 2013.
George, G.A., et al., "Cure Monitoring of Aerospace Epoxy Resins and Prepregs by Fourier Transform Infrared Emission Spectroscopy," Polymer International 41(2):169-182, Oct. 1996.
Grynkiewicz, G. et al., "A New Generation of $Ca^{2+}$ Indicators With Greatly Improved Fluorescence Properties," Journal of Biological Chemistry 260(6):3440-3450, Mar. 1985.

Hanson, G.T., et al., "Green Fluorescent Protein Variants as Ratiometric Dual Emission pH Sensors. 1. Structural Characterization and Preliminary Application," Biochemistry 41(52):15477-15488, Dec. 2002.
Heyes, A.L., et al., "Two-Colour Phosphor Thermometry for Surface Temperature Measurement," Optics & Laser Technology 38(4-6):257-265, Jun.-Sep. 2006.
Howie, T., et al., "Thermal Damage Detection of CFRP Using Coatings Doped With Fluorescent Probes," Proceedings of the 2013 International SAMPE Technical Conference, Long Beach, Calif., May 6-9, 2013, pp. 2204-2214.
Howie, T., et al., "Time-Temperature Indicator for Evaluating Incipient Thermal Damage of CFRP," Proceedings of the 2014 International SAMPE Technical Conference, Jun. 2-5, 2014, Seattle, 16 pages.
Howie, T.L., "Detection of Incipient Thermal Damage of Carbon Fiber/Epoxy Composites Using Fluorescent Thermal Damage Probes," doctoral dissertation, 2013, University of Washington, Seattle, 152 pages.
Hu, J., and S. Liu, "Responsive Polymers for Detection and Sensing Applications: Current Status and Future Developments," Macromolecules 43(2):8315-8330, Oct. 2010.
Inouye, M., et al., "New Thermo-Response Dyes: Coloration by the Claisen Rearrangement and Intramolecular Acid-Base Reaction," Angewandte Chemie International Edition in English 31(2):204-205, Nov. 1992.
Kalambet, Y., et al., "Reconstruction of Chromatographic Peaks Using the Exponentially Modified Gaussian Function," Journal of Chemometrics 25(7):352-356, Jul. 2011.
Kinami, M., et al., "Polyesters With Built-in Threshold Temperature and Deformation Sensors," Chemistry of Materials 18(4):946-955, Jan. 2006.
Kumar, P., and B. Rai, "Delaminations of Barely Visible Impact Damage in CFRP Laminates," Composite Structures 23(4):313-318, 1993.
Kunzelman, J., et al., "Pressure-Sensitive Chromogenic Polyesters," Macromolecular Materials and Engineering 294(4):244-249, Apr. 2009.
Le Bras, M., et al., "The Degradation Front Model—A Tool for the Chemical Study of the Degradation of Epoxy Resins in Fire," Journal of Fire Sciences 14(3):199-234, May-Jun. 1996.
Lee, B.S., et al., "Polymer-Based Time-Temperature Indicator for High Temperature Processed Food Products," Food Science and Biotechnology 21(5):1483-1487, Oct. 2012.
Lesnikovich, A.I., and S.V. Levchik, "A Method of Finding Invariant Values of Kinetic Parameters," Journal of Thermal Analysis 27(1):89-94, 1983.
Levchik, S.V., et al., "Analysis and Development of Effective Invariant Kinetic Parameters Finding Method Based on the Non-Isothermal Data," Thermochimica Acta 92:157-160, Sep. 1985.
Lévêque, D., et al., "Analysis of How Thermal Aging Affects the Long-Term Mechanical Behavior and Strength of Polymer-Matrix Composites," Composites Science and Technology 65(3-4):395-401, Mar. 2005.
Li, S., et al., "Cross-Linking Kinetics and Swelling Behaviour of Aliphatic Polyurethane," Polymer 41(15):5571-5576, Jul. 2000.
Life Technologies, "Indo-1 Calcium Indicator," Life Technologies, Mar. 2013, <https://web.archive.org/web/20130218204224/http://www.invitrogen.com/site/us/en/home/Products-and-Services/Applications/Drug-Discovery/Target-and-Lead-Identification-and-Validation/g-protein_coupled_html/cell-based-second-messenger-assays/indo-1-calcium-indicator.html> [retrieved Oct. 21, 2016], 2 pages.
Lin, K.-F-., and F.W. Wang, "Fluorescence Monitoring of Polarity Change and Gelation During Epoxy Cure," Polymer 35(4):687-691, 1994.
Löwe, C., and C. Weder, "Oligo(p-phenylene Vinylene) Excimers as Molecular Probes: Deformation-Induced Color Changes in Photoluminescent Polymer Blends," Advanced Materials 14(22):1625-1629, Nov. 2002.
Mailhot, B., et al., "Study of the Degradation of an Epoxy/Amine Resin, 2: Kinetics and Depth-Profiles," Macromolecular Chemistry and Physics 206(5):585-591, Mar. 2005.

(56) References Cited

OTHER PUBLICATIONS

Mailhot, B., et al., "Study of the Degradation of an Epoxy/Amine Resin, 1: Photo- and Thermo-Chemical Mechanisms," Macromolecular Chemistry and Physics 206(5):575-584, Mar. 2005.

Matzkanin, G.A., and G.P. Hansen, "Heat Damage in Graphite Epoxy Composites: Degradation, Measurement and Detection," Report No. NTIAC-SR-98-02, vol. 4, No. 3, <http://www.ndt.net/article/v04n03/ntiac/ntiac.htm> [retrieved Oct. 21, 2016], 4 pages.

Morton, J., and E.W. Godwin, "Impact Response of Tough Carbon Fibre Composites," Composite Structures 13(1):1-19,1989.

Musto, P., "Two-Dimensional FTIR Spectroscopy Studies on the Thermal-Oxidative Degradation of Epoxy and Epoxy-Bis(maleimide) Networks," Macromolecules 36(9):3210-3221, Apr. 2003.

Musto, P., et al., "Thermal-Oxidative Degradation of Epoxy and Epoxy-Bismaleimide Networks: Kinetics and Mechanism," Macromolecular Chemistry and Physics 202(18):3445-3458, Dec. 2001.

Natrajan, V.K., and K.T. Christensen, "Two-Color Laser-Induced Fluorescent Thermometry for Microfluidic Systems," Measurement Science and Technology 20(1):015401, Jan. 2009.

Oleinik, E.F., "Epoxy-Aromatic Amine Networks in the Glassy State Structure and Properties," Advances in Polymer Science, Epoxy Resins and Composites IV 80:49-99, 1986.

Oleinik, E.F., et al., "Evolution in Concepts Concerning the Mechanism of Plasticity in Solid Polymers After the 1950s," Polymer Science, Series A 49(12):1302-1327, Dec. 2007.

Oleynik, E., "Plastic Deformation and Mobility in Glassy Polymers," Progress in Colloid & Polymer Science 80:140-150, 1989.

Olmos, D., et al., "Kinetic Study of Epoxy Curing in the Glass Fiber/Epoxy Interface Using Dansyl Fluorescence," Journal of Colloid and Interface Science 267(1):117-126, Nov. 2003.

Olshenske, Z., et al., "Overview of NAVAIR NDI Programs for Composite Heat Damage Assessment," Proceedings of the 2010 International SAMPE Technical Conference, Seattle, May 17-20, 2010 (CD-ROM), 19 pages.

Paik, H.-J., and N.-H. Sung, "Fiberoptic Intrinsic Fluorescence for In-Situ Cure Monitoring of Amine Cured Epoxy and Composites," Polymer Engineering and Science 34(12):1025-1032, Jun. 1994.

Patterson-Jones, J.C., and D.A. Smith, "The Thermal Degradation of an Amine-Cured Epoxide Resin at Temperatures Between 200° C. and 310° C.," Journal of Applied Polymer Science 12(7):1601-1620, Jul. 1968.

Peng, X., et al., "Colorimetric and Ratiometric Fluorescence Sensing of Fluoride: Tuning Selectivity of Proton Transfer," Journal of Organic Chemistry 70(25):10524-10531, Nov. 2005.

Peng, X., et al., "Fluorescence Ratiometry and Fluorescence Lifetime Imaging: Using a Single Molecular Sensor for Dual Mode Imaging of Cellular Visocosity," Journal of the American Chemical Society 133(17):6626-6635, Apr. 2011.

Poon, C., et al., "Assessment of Impact Damage in Toughened Resin Composites," Theoretical and Applied Fracture Mechanics 13(2):81-97, May 1990.

Pucci, A., et al., "Polymer Composites With Smart Optical Properties," Soft Matter 7(8):3689-3700, 2011.

Quinson, R., et al., "Components of Non-Elastic Deformation in Amorphous Glassy Polymers," Journal of Materials Science 31(16):4387-4394, Jan. 1996.

Rigail-Cedeño, A., and C.S.P. Sung, "Fluorescence and IR Characterization of Epoxy Cured With Aliphatic Amines," Polymer 46(22):9378-9384, Oct. 2005.

Rose, N., et al., "Thermal Oxidative Degradation of Epoxy Resins: Evaluation of Their Heat Resistance Using Invariant Kinetic Parameters," Polymer Degradation and Stability 45(3):387-397, 1994.

Rouquie, S., et al., "Thermal Cycling of Carbon/Epoxy Laminates in Neutral and Oxidative Environments," Composites Science and Technology 65(3-4):403-409, Mar. 2005.

Sathish, S., et al., "Development of Nondestructive Non-Contact Acousto-Thermal Evaluation Technique for Damage Detection in Materials," Review of Scientific Instruments 83(9):095103, Sep. 2012, 12 pages.

Sathish, S., et al., "Thermo-Elastic Characterization of Heat Damage in Carbon Fiber Epoxy Composites," Review of Quantitative Nondestructive Evaluation 25:1015-1019, 2006.

Scheenen, W.J.J.M., et al., "Photodegradation of Indo-1 and Its Effect on Apparent $Ca^{2+}$Concentrations," Chemistry & Biology 3(9):765-774, Sep. 1996.

Schieffer, A., et al., "A Coupled Analysis of Mechanical Behaviour and Ageing for Polymer-Matrix Composites," Composites Science and Technology 62(4):543-549, Mar. 2002.

Schwartz, M., "Figure 1. Application of a TTI as a Food Quality Monitor (19)," in "Encyclopedia of Smart Materials, vol. 1 and vol. 2," John Wiley & Sons, Inc., New York, 2002, p. 178.

"Serafim Nikolaevich Zhurkov (May 29, 1905-Sep. 18, 1997)," Physics of the Solid State 47(5):797-800, May 2005 (translated from the Fizika Tverdogo Tela 47(5):771-776, May 2005).

Shelley, P.H., et al., "Handheld Infrared Spectroscopy for Composite Non-Destructive Testing," Proceedings of the 2011 International SAMPE Technical Conference, Long Beach, Calif., May 23-26, 2011, 14 pages.

Sing, C.E, et al., "Time-Temperature Indicators for High Temperature Applications," Journal of Materials Chemistry 19(1):104-110, 2009.

Song, J.C., and C.S.P. Sung, "Fluorescence Studies of Diaminodiphenyl Sulfone Curing Agent for Epoxy Cure Characterization," Macromolecules 26(18):4818-4824, Aug. 1993.

Street, K.N., et al., "Thermal Damage Effects on Delamination Toughness of a Graphite/Epoxy Composite," Composites Science and Technology 32:1-14, 1988.

Sung, C.S.P., et al., "Characterization of Epoxy Cure by UV-Visible and Fluorescence Spectroscopy: Azochromophoric Labeling Approach," Macromolecules 19(12):2922-2932, Dec. 1985.

Sung, C.S.P., et al., "A Novel Fluorescence Technique for Monitoring Cure Reactions in Epoxy Networks," Macromolecules 18(7):1510-1512, Jul. 1985.

Tandon, G.P., and K.V. Pochiraju, "Heterogeneous Thermo-Oidative Behavior of Multidirectional Laminated Composites," Journal of Composite Materials 45(4):415-435, Feb. 2011.

Tandon, G.P., and W.R. Ragland, "Influence of Laminate Lay-Up on Oxidation and Damage Growth: Isothermal Aging," Composites Part A: Applied Science and Manufacturing 42(9):1127-1137, Sep. 2011.

Tang, L., et al., "Stimuli-Responsive Epoxy Coatings," Applied Materials & Interfaces 1(3):688-696, Feb. 2009.

Taylor, D.M., and K.Y. Lin, "Aging Effects on the Interlaminar Shear Strength of High-Performance Composites," Journal of Aircraft 40(5):971-976, Sep.-Oct. 2003.

Toivola, R., et al., "Damage Detection for Aerospace Composites Using Matrix Resins Functionalized With Fluorescent Probe Molecules," Proceedings of 44th International SAMPE Technical Conference, Charleston, S.C., Oct. 22-25, 2012, 14 pages.

Treinin, A., and E. Hayon, "Absorption Spectra and Reaction Kinetics of $NO_2$, $N_2O_3$, and $N_2O_4$ in Aqueous Solution," Journal of the American Chemical Society 92(20):5821-5828, Oct. 1970.

Tsironi, T., et al., "Predictive Modelling and Selection of Time Temperature Integrators for Monitoring the Shelf Life of Modified Atmosphere Packed Gilthead Seabream Fillets," LWT—Food Science and Technology 44(4):1156-1163, May 2011.

Tsotsis, T.K., "Thermo-Oxidative Aging of Composite Materials," Journal of Composite Materials 29(3):410-422, Feb. 1995.

Tyler, D.R., "Mechanistic Aspects of the Effects of Stress on the Rates of Photochemical Degradation Reactions in Polymers," Journal of Macromolecular Science, Part C—Polymer Reviews 44(4):351-388, 2004.

Van Keuren, E., et al., "Three-Dimensional Thermal Imaging Using Two-Photon Microscopy," Journal of Physics D: Applied Physics 37(20):2938-2943, Sep. 2004.

Wang, F.W., et al., "Novel Fluorescence Method for Cure Monitoring of Epoxy Resins," Polymer 27(10):1529-1532, Oct. 1986.

(56) References Cited

OTHER PUBLICATIONS

Woo, H.Y., et al., "Solvent Effects on the Two-Photon Absorption of Distyrylbenzene Chromophores," Journal of the American Chemical Society 127(42):14721-14729, Sep. 2005.

Wu, D., et al., "Preliminary Study on Time-Temperature Indicator (TTI) System Based on Urease," Food Control 34:230-234, 2013.

Yamamoto, S., et al., "In Situ Observation of Thermochromic Behavior of Binary Mixtures of Phenolic Long-Chain Molecules and Fluoran Dye for Rewritable Paper Application," Crystal Growth & Design 8(7):2256-2263, Jun. 2008.

Yang, J., et al., "Excimer Formation in Uniaxially Stretched Polymer Films," Journal of Applied Polymer Science 82(10):2347-2351, Dec. 2001.

Ye, Q. et al., "Characterization of Photopolymerization of Dentin Adhesives as a Function of Light Source and Irradiance," Journal of Biomedical Materials Research B 80(2):440-446, Feb. 2007.

Yoshino, K., et al., "Photoconductivily of Poly(3-alkylthiophene) in Solid and Liquid States," Japanese Journal of Applied Physics 28(6):L1029-L1031, Jun. 1989.

Yousuf, A., and P. Kulowitch, "Detecting Heat Damage in Composites Using Laser Induced Fluorescence," Proceedings of the 2000 ASEE Annual Conference, Jun. 18-21, 2000, St. Louis, Missouri, Session 2559, pp. 5.160.1-5.160.9.

Yu, W., et al., "Rapid Determination of Renal Filtration Function Using an Optical Ratiometric Imaging Approach," American Journal of Physiology—Renal Physiology 292(6):F1873-F1880, Jun. 2007.

Zhu, H., et al., "Dual-Emission of a Fluorescent Graphene Oxide—Quantum Dot Nanohybrid for Sensitive and Selective Visual Sensor Applications Based on Ratiometric Fluorescence," Nanotechnology 23(31):315502, Aug. 2012.

Zhurkov, S.N., and V.E. Korsukov, "Atomic Mechanism of Fracture of Solid Polymers," Journal of Polymer Science, Part B—Polymer Physics 12(2):385-398, Feb. 1974.

* cited by examiner

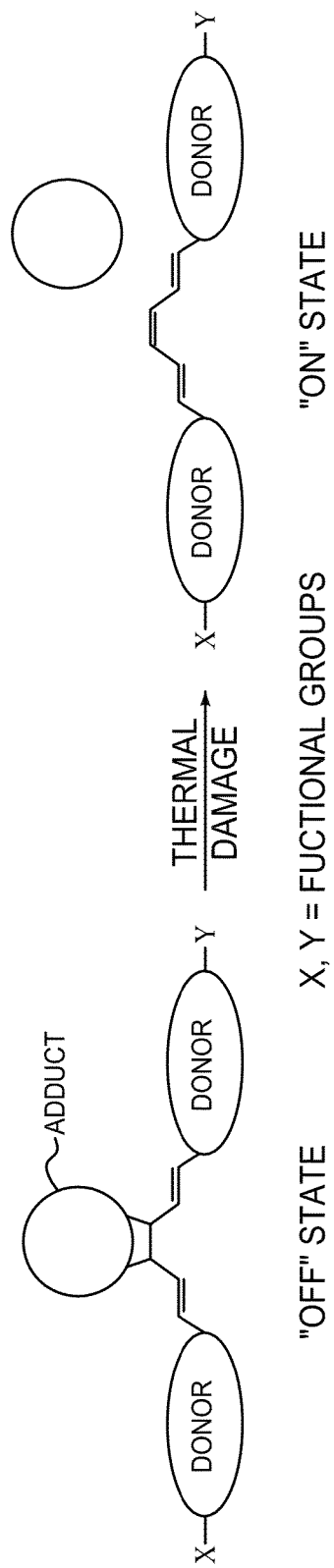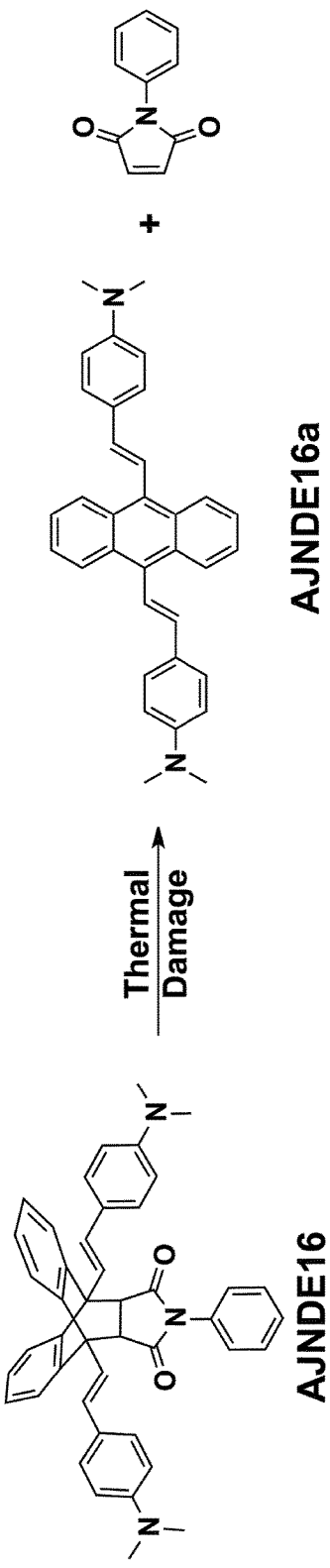
FIG. 1A
FIG. 1B

DETECTION OF THERMAL DAMAGE OF COMPOSITES USING MOLECULAR PROBES

CROSS-REFERENCES TO RELATED APPLICATIONS

This application claims the benefit of U.S. Provisional Application No. 61/818,315, filed May 1, 2013, and U.S. Provisional Application No. 61/916,063, filed Dec. 13, 2013, the disclosures of which are hereby incorporated by reference in their entirety.

JOINT RESEARCH AGREEMENT

The claimed configurations set forth herein were made as a result of activities undertaken within the scope of a joint research agreement. The parties to the joint research agreement are (1) University of Washington and (2) Boeing.

BACKGROUND

Carbon-fiber reinforced plastic composites (CFRP) have seen increasing use as structural components in aircraft due to their high specific stiffness and strength. One issue with the use of CFRP is that thermal degradation of the matrix can lead to significant decreases in the glass transition temperature, mechanical properties such as flexural strength, compression after impact (CAI), and interlaminar shear strength, and cause delaminations, fiber-matrix debonding, and embrittlement and cracking of the matrix. For aircraft this thermal damage can come from sources such as fires, lightning strikes, ground-reflected efflux from the engines, accidents, etc. Of even greater concern is that below a certain threshold exposure level, the part may appear visibly undamaged and it can also appear undamaged to common nondestructive evaluation (NDE) methods such as ultrasound techniques, but the part can exhibit up to 60% loss of strength. This type of damage is often termed incipient thermal damage.

Many different techniques have been utilized to try to evaluate and detect incipient thermal damage to CFRP parts including FTIR, laser-induced fluorescence (LIF), Raman spectroscopy, and NMR. While many of the techniques have been shown capable of detecting incipient thermal damage most of them are not viable options for inspection of parts in service. Currently the most prominent means of detecting incipient thermal damage for in service inspection is diffuse reflectance infrared Fourier transform spectroscopy (DRIFT). DRIFT spectroscopy is capable of detecting and providing quantitative information changes to the functional groups of the matrix which are affected as the matrix thermally degrades. Changes in the carbonyl and phenol bands of the FTIR spectrum were found to correlate fairly well with changes to mechanical properties such as ILSS and were sensitive to early signs of thermal oxidation before significant strength loss occurred. One of the main issues with DRIFT spectroscopy though is that it has a very small effective inspection area relative to the size of many aerospace parts so it is not a very efficient wide-area technique. As a result it can be difficult to locate and evaluate thermal damage sites on large CFRP parts if the damage site is not already known. Another method that showed promise as a wide-area inspection technique for incipient thermal damage was laser-induced fluorescence (LIF). LIF works by using a laser excitation source to excite the autofluorescence of the matrix. It has been found that both the intensity and the wavelength at the max intensity $\lambda_{max}$, change as a result of thermal damage, however only the $\lambda_{max}$ was shown to correlate directly to changes in mechanical properties such as flexural strength. Both DRIFT and LIF are only surface sensitive techniques however, so considerable testing needs to be done to determine how well they apply to bulk materials. Thermo-elastic characterization has been shown as possible method for detecting volumetric thermal degradation. Thermo-elastic characterization works by using an acoustic horn to generate a high amplitude acoustic wave that generates heat as it passes through the material and an IR camera is used to measure the change in temperature. Potential thermal damage can be observed by changes in the slope of temperature over the amplitude of the wave ($\Delta T/\Delta A$). Thermo-elastic characterization has also shown good potential for finding incipient thermal damage however, there is very little literature available so it is difficult to evaluate its applicability to in field use.

A common issue with all of these inspection methods (except for LIF) is that while they are capable of detecting thermal damage on a sample, they are not very efficient for inspecting large parts if the damage location is not known. Because incipient thermal damage of CFRP can be very difficult to locate visually, this can be a problem for inspecting large aircraft parts for thermal damage quickly. Therefore, improved inspection methods for incipient thermal damage of CFRP are desired.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a method of monitoring thermal exposure of a composite is provided. In one embodiment, the method comprises:
  (a) providing a composite, comprising:
    (i) a matrix; and
    (ii) a first probe, wherein the first probe is not luminescent until activated by heat to a temperature above 200° C., after which it becomes luminescent and has a first luminescence profile;
  (b) exposing the composite to a time-temperature profile that includes a portion of time at a temperature above 200° C.; and
  (c) measuring an optical property of the composite.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A schematically illustrates the fluorescent activation mechanism of a molecule in accordance with the disclosed embodiments.

FIG. 1B illustrates a process for activation of fluorescence in a representative molecule in accordance with the disclosed embodiments.

DETAILED DESCRIPTION

Figure 1C:
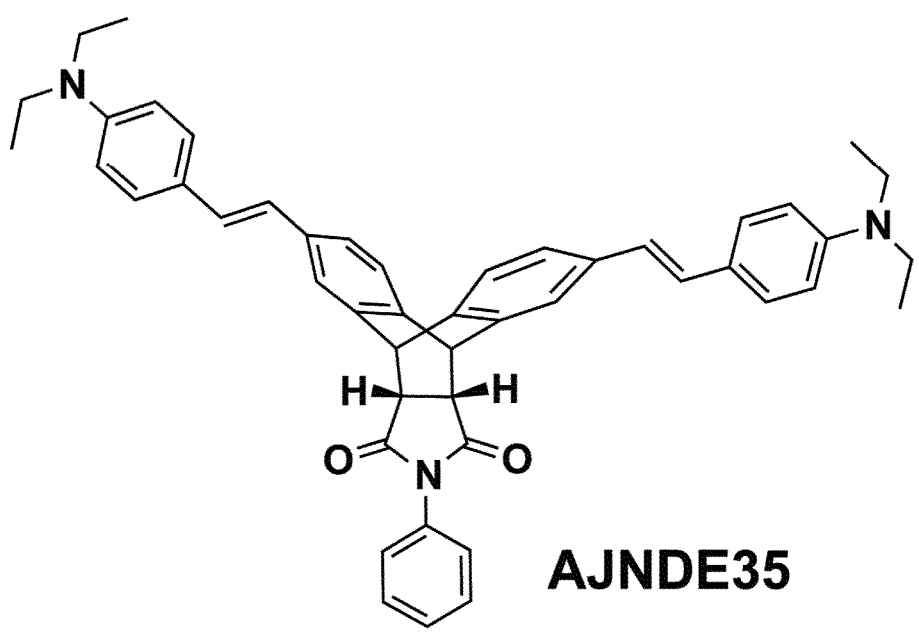
FIG. 1C illustrates a representative molecule that can be activated to be fluorescent in accordance with the disclosed embodiments.

Improved methods of detecting thermal exposure are provided herein. The provided methods utilize initially dormant luminescent probes incorporated into a matrix to form a composite. When exposed to heat over a period of time (a "time-temperature profile"), the luminescent probes are "activated" through a molecular transformation initiated by thermal energy. The activated probes are luminescent and exhibit a luminescence profile based on the extent of thermal exposure, thereby providing an indicator of the thermal exposure experienced by the matrix. When the composite is used to produce a structural component of a vehicle (e.g., an aircraft), the methods provide a convenient, large-area indicator of thermal damage experienced by the structural component.

In one aspect, a method of monitoring thermal exposure of a composite is provided. In one embodiment, the method comprises:
  (a) providing a composite, comprising:
    (i) a matrix; and
    (ii) a first probe, wherein the first probe is not luminescent until activated by heat to a temperature above 200° C., after which it becomes luminescent and has a first luminescence profile;
  (b) exposing the composite to a time-temperature profile that includes a portion of time at a temperature above 200° C.; and
  (c) measuring an optical property of the composite.

The method begins with a step of providing a composite. The composite includes both a matrix and a first probe. The matrix can be any material capable of supporting the first probe without detrimental impact on its luminescent properties. In one embodiment, the matrix is selected from the group consisting of a thermoset polymer, a thermoplastic polymer, and a sol-gel. A typical matrix is a polymer of the types used to form carbon-fiber reinforced plastic composite. Representative polymer matrix materials include classes of two-part epoxy resins, such as Hysol EA 9390, Araldite MY 720/Aradur 976, or Toray 3900 with various amine based curing agents (e.g. 2,2'-Dimethyl-4,4'methylenebis (cyclohexylamine)).

In one embodiment, the matrix further comprises carbon fibers or other structural additives (e.g., nanoparticles). When carbon fibers are included in the matrix a carbon-fiber reinforced plastic composite (CFRP) can be formed. CFRPs can be used in various structural applications, as known to those of skill in the art. Particularly, the composite can be used in certain embodiments as a structural component of a vehicle, such as an aircraft or automobile. Specific locations on a vehicle that would benefit from the composite include areas subject to high temperatures, such as near engines and exhaust outlets.

The first probe forms the second part of the composite. In one embodiment, the probe is incorporated within the matrix. In such an embodiment, the first probe can be integrated into the matrix to form the composite. Such integration is typically accomplished by mixing the first probe into the matrix material, or precursor thereof, during formation of the composite. For example, if a two-part epoxy is used to form the matrix, the first probe can be mixed into one of the two parts of the epoxy (in liquid form), or mixed into the combined parts of the epoxy when still in liquid form, prior to polymerization of the epoxy to form a solid composite. Such methods are described in the EXAMPLES below. Despite these specific examples, it will be appreciated that any technique capable of incorporating the first probe into the matrix is contemplated by the present disclosure.

When the first probe (and any second and further probes) are incorporated into the matrix it is an important design consideration that the matrix be optically transparent enough to excite probes and to detect a fluorescence signal from the probes at the wavelengths of light related to the excitation of and emission from the first (and subsequent) probes. Therefore, if the first probe has an emission wavelength of 500 nm, the matrix must be relatively transparent at the emission wavelength. Without this relationship, emission of the first probe will be attenuated by the matrix and measurements related to the first probe will be inaccurate.

In one embodiment, a coating on the matrix comprises the first probe. Instead of, or in addition to, mixing the first probe into the matrix, the first probe can be applied to a surface of the matrix as a coating. Such a coating may comprise a host material (e.g., a polymer) that supports the first probe (by being chemically and optically compatible) and can be applied to the surface of the matrix. Such a supported first probe can be coated onto the matrix by any film-forming technique (e.g., painting techniques) known to those of skill in the art, such as spray coating, brush coating, and the like. Representative coating host materials include polymers of the same general types described above with regard to the matrix.

The first probe is not luminescent until activated by heat to a temperature above 200° C., after which it becomes luminescent and has a first luminescence profile. The thermal activation of luminescence is achieved through a thermally induce chemical mechanism whereby an "adduct"

moiety is removed. Upon removal of the adduct the first probe transitions from a non-luminescent "off" state to a luminescent "on" state. While the first probe may have some small level of luminescence in the off state, there is a dramatic rise in luminescence in the on state. For example, the on state may have at least an order of magnitude increase in luminescence intensity compared to the off state.

An example of the activation mechanism is depicted schematically in FIG. 1A, which illustrates a donor-donor compound with a conjugated link between the donors. Functional groups X and Y can be the same or different and partially define the luminescent properties, as well as other properties (e.g., solubility in matrix materials). A specific activation mechanism is illustrated in FIG. 1B, with reference to the molecule referred to herein as AJNDE16, which is activated by thermal energy (a time-temperature profile) to release an adduct and form AJNDE16a, which is fluorescent. AJNDE16, as well as AJNDE35 (illustrated in FIG. 1C), are described in more detail below in the EXAMPLES. While representative probe compounds are described herein, it will be appreciated that the disclosed embodiments are not limited to the exemplary compounds. Instead, any compound capable of meeting the recited requirements of the first probe can be used.

The activation of the first probe occurs at a temperature above 200° C. Known probes are activated at temperatures below 200° C., which greatly limits the ability of such probes to be used to detect incipient thermal damage of the type experienced in, for example, aircraft having CFRP structural members. By activating only at relatively high temperatures, above 200° C., the first probe of the disclosed method allows for detection of incipient thermal damage in such CFRP structural members and other similar applications. In one embodiment, the first probe is activated at a temperature above 200° C. and below 300° C. Such a probe is capable of testing for thermal damage across this temperature range.

The first probe is luminescent, demonstrating stimulated emission. In one embodiment, the first probe is fluorescent or phosphorescent. The first probe is excited by a probe wavelength (or range of wavelengths) and emits a luminescence profile, which may include one or more peak emission wavelengths, as well as a range of non-peak wavelengths. In one embodiment, the matrix is transparent at wavelengths within the first luminescence profile.

Figure 2A:
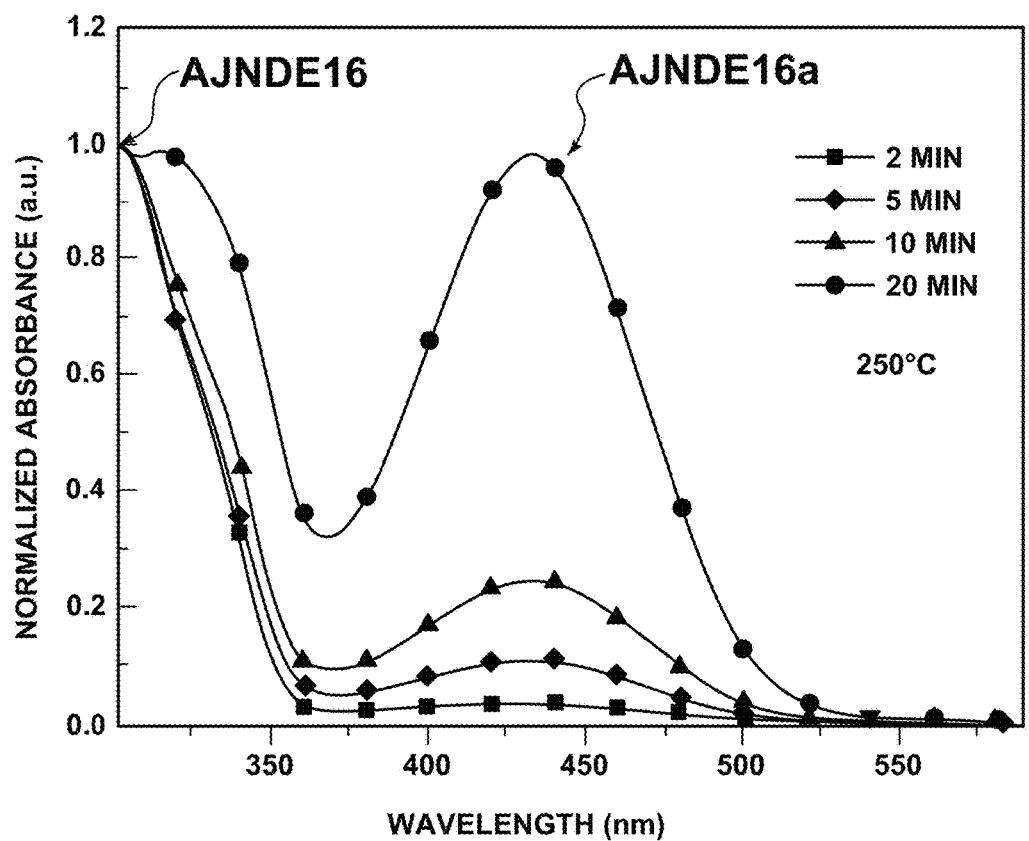
FIG. 2A. Kinetics study of AJNDE16 heated at 250° C. monitored by UV absorption spectra.

Exemplary wavelength profiles are disclosed in the EXAMPLES section (e.g., FIG. 2A illustrating the effect of a time-temperature profile on AJNDE16).

The method proceeds with a second step of exposing the composite to a time-temperature profile that includes a portion of time at a temperature above 200° C. This step of the method involves the application of thermal energy to the composite using a time-temperature profile. Such thermal energy may result in thermal damage, for example, the use of the composite in an application where it may be subjected to temperatures above 200° C., which may cause incipient thermal damage (e.g., use of a CFRP on an operating aircraft body or during repairs that involve exposure to high temperatures).

The time-temperature profile is a temperature or series of temperatures applied over a defined period of time (e.g., from a first time to a second time), which results in an amount of thermal energy applied to the composite. The time-temperature profile can be a constant temperature rise, a constant temperature decline, a periodic temperature variation (e.g., temperature cycling), or non-uniform temperature variation. The time-temperature profile can be defined as a temperature ramp from a first temperature ($T_1$) to a second temperature ($T_2$), or further temperatures $T_x$, etc. can be used to define the time-temperature profile.

In many practical implementations of the method, the time-temperature profile will result from the temperatures experienced by a vehicle on which the composite is mounted (e.g., as a structural member). In such situations, it is unlikely that the time-temperature profile will be a uniform rise, or even periodic variations; instead, the temperatures will likely rise and fall non-uniformly as the vehicle is operated.

The method concludes with a step of measuring an optical property of the composite. Given the emphasis of the method on ease of use and applicability to large-area applications, optical methods are well suited for such analyses. In one embodiment, the optical property is stimulated emission of the first probe. As discussed above, luminescent probes can be used, which then require the use of a technique capable of measuring luminescence. Representative analytical techniques for measuring the optical property include any fluorescence or phosphorescence detection methods. Such methods include spectroscopic methods and imaging methods (e.g., use of a CCD camera in conjunction with an appropriate excitation light source), which are generally known to those of skill in the art.

The measured optical property indicates the extent of exposure of the first probe—and therefore the composite—to the time-temperature profile.

The optical property may provide a general indication of the effect of the time-temperature profile on the composite. For example, if the optical property is fluorescence and the time-temperature profile includes a temperature above 200° C., then the composite can be quickly analyzed for fluorescence by illuminating the composite with the appropriate wavelength of light that will induce fluorescence in the first probe if it has been activated by the time-temperature profile. This type of gross analysis can provide a simple yes or no determination with regard to thermal damage experienced by the composite.

To obtain more specific information about the thermal damage resulting from the time-temperature profile, in one embodiment, the method further comprises a step of analyzing the optical property to determine thermal exposure of the composite. In this step a more detailed optical analysis is performed, such as quantitative luminescence spectroscopy, in order to determine the exact impact of the time-temperature profile on the first probe. The resulting spectroscopic data may yield information about the specific temperatures and exposure times of the time-temperature profile.

In a further embodiment, the step of analyzing the optical property comprises comparing the optical property to a calibration data set. By determining the characteristics of the first probe under a variety of time-temperature profiles in a controlled manner, a calibration data set can be obtained for any probe. The luminescence of a probe is affected based on temperatures and exposure times, such that the luminescent characteristics (e.g., intensity, wavelength, etc.) can be mapped for a time-temperature profile to provide the calibration data set. This calibration data set can be obtained either before or after the first probe is measured in the composite. Once both the optical property and the calibration data set are obtained, the two can be compared and the time-temperature profile can be characterized based on the optical property. This information leads to a conclusion regarding the thermal damage experienced by the composite.

In one embodiment, the composite further comprises a second probe, wherein the second probe is not luminescent until activated by heat, after which it becomes luminescent and has a second luminescence profile that is different from the first luminescence profile. In one embodiment the second probe is activated at a temperature above 200° C. In another embodiment the second probe is activated at a temperature below 200° C.

Integrating a second probe into the composite allows for additional characterization of the time-temperature profile with regard to thermal damage experienced by the composite. In this regard, because the second probe is different in composition than the first probe it has a different luminescence profile that can be characterized separate from, or in combination with, the first luminescence profile. Accordingly, in one embodiment, the optical property is the combined stimulated emission of the first probe and the second probe.

In one embodiment, the first probe and the second probe combine to be a time-temperature indicator (TTI) of thermal damage. While a single probe can be used to determine certain aspects of the time-temperature profile, by using a second probe that is affected differently by temperature over time, a true TTI analysis can be performed, which determines not only the temperatures reached but also the duration of those exposures. Alternatively, a probe that is not affected by temperature can be used as a reference probe for the first probe in order to enable TTI analysis. In general, the first probe can be used for TTI analysis as long as a reference probe is provided that provides the relative change in the amount of the first probe activated by temperature.

EXAMPLE 2 provides an exemplary system that includes two different probes that combine in a composite to provide more detailed information about thermal damage to the composite as a TTI.

The second probe can be incorporated into the matrix or applied as a coating, similar to the first probe. Typically the first probe and the second probe will be utilized in the same capacity, either within the matrix or applied as a coating. However, in certain embodiments the first probe is incorporated into the composite in either the matrix or as a coating, while the second probe is incorporated into the composite in the other of the matrix or the coating.

Subsequent probes beyond the first and second probes can also be used, in a similar manner, to provide additional tools for characterizing the time-temperature profile and related thermal damage.

The following examples are included for the purpose of illustrating, not limiting, the described embodiments.

EXAMPLES

Example 1. Detection of Incipient Thermal Damage

1. Introduction

In this Example, the use of a fluorescent thermal damage probe incorporated into an epoxy matrix is utilized as means of locating potential thermal damage sites in a composite material. The fluorescence emission of the dye is activated by a combination of time and temperature in the temperature range were incipient thermal damage can be significant. Using the appropriate excitation source the dye does not emit fluorescence until it is activated allowing it to provide a large contrast between the "on" and "off" state that can be observed relatively easily by visual inspection.

2. Experimentation 2.1 Sample Preparation of Thermal Damage Probe in Epoxy Resin Hysol EA 9390 Part A (epoxy resin) and Part B (curing agent) were mixed by hand in a ratio of 100:56 parts by weight. In this Example this batch will be referred to as neat epoxy. Both Part A and Part B were made by Henkel Corporation and used as-received. 0.05 wt % of the probe AJNDE16 (FIG. 1B) was added to another batch of epoxy with the same mixing ratio of resin to curing agent as the neat epoxy. This batch will be referred to as probe doped epoxy. A small portion of both resins was spin coated onto glass substrates at speeds between 3500 and 4000 rpm to form thin films. The films were then cured at 121° C. (250° F.) for 2.5 hours in a Thermo Scientific Heratherm Advanced Protocol mechanical convection oven.

The remaining epoxy from both the neat epoxy and the probe doped epoxy was used to wet-layup composite panels with 3 plies of T800 plain weave carbon fiber fabric (Toray). After the wet lay-up the composite panels were processed by conventional vacuum bag process and cured in an autoclave at 121° C. (250° F.) for 2.5 hours.

2.2 Heat-treatment of Thin Films

The thin films of neat epoxy and the probe doped epoxy were subjected to heat-treatments at temperatures of 204° C. (400° F.), 232° C. (450° F.), and 260° C. (500° F.) in the convection oven. The films were removed from the oven at certain intervals to measure the fluorescence and UV-Visible absorption spectra. After the measurements were made the thin-films were placed back into the oven at the same temperature and this process was repeated until the fluorescence of the sample was no longer distinguishable from the noise in the baseline.

2.3 Thin Film Fluorescence Measurements

Fluorescence measurements were made on a Stellarnet BlueWave UVN spectrometer with a R600-8-UVVIS SR reflectance probe. The probe contains a 600 μm read fiber (detector) at the core and is surrounded by 7 fibers that focus the excitation source onto the sample. A blue 470 nm LED was used as the excitation source for the fluorescence measurements. The probe was at a 45° angle to the surface of the sample and the bottom portion of the probe rested on surface of the sample to try to reduce the effects of variations in the thickness of the samples on the distance to probe. The integration time for the detector was set to 2000 ms and 9 scans of each spectrum were averaged. Samples were cooled to room temperature after heat-treatment before the fluorescence spectra were measured.

2.4 UV-Visible Absorption Spectra

UV-Vis spectra of the thin films of both the neat epoxy and the probe doped epoxy were measured from 250 to 900 nm at a scan rate of 240 nm/min using a Thermo Scientific Evolution 300. An uncoated glass substrate was used as the reference. Samples had been cooled to room temperature after heat-treatments before the spectra were measured.

3. Results 3.1 Design of Thermal Damage Probes

To be an efficient and reliable tool to detect the thermal damage of CFRP, the probing molecule is required to respond to the proper temperature window. From the molecular level point of view, dynamic covalent chemistry and non-covalent intermolecular interactions, triggered at elevated temperatures, generally offer intriguing opportunities in inducing fluorescence change. Typically, non-covalent interactions are generally more susceptible to the external environmental factors, and thus kinetically labile. In this sense, thermally induced covalent chemistry is the more suitable and reliable approach to design efficient fluorescent molecular probes for detection and evaluation of the thermal damage on a CFRP samples. Moreover, it has been generally accepted that the thermal damage in epoxy matrix CFRP due to fires, lightning strikes, ground-reflected efflux from the engines, accidents, etc. is related to high temperatures of above 200° C. on CFRP. Development of thermochromic molecular probes operating at this temperature range is a major challenge since most of fluorescent molecules are not thermochemically stable at such temperatures. On the other hand, there are few chemical reactions that can be applied to induce fluorescence changes before and after the reactions as long as molecular structures of derivatives of the probes after the high temperature exposure can be stabilized. Thermochromic molecule AJNDE16 as illustrated in FIG. 1B has been designed and synthesized accordingly. As shown, when treated at elevated temperatures, AJNDE16 undergoes a chemical reaction to release a highly fluorescent activated molecule AJNDE16a. AJNDE16a was synthesized independently for comparison.

Figure 2B:
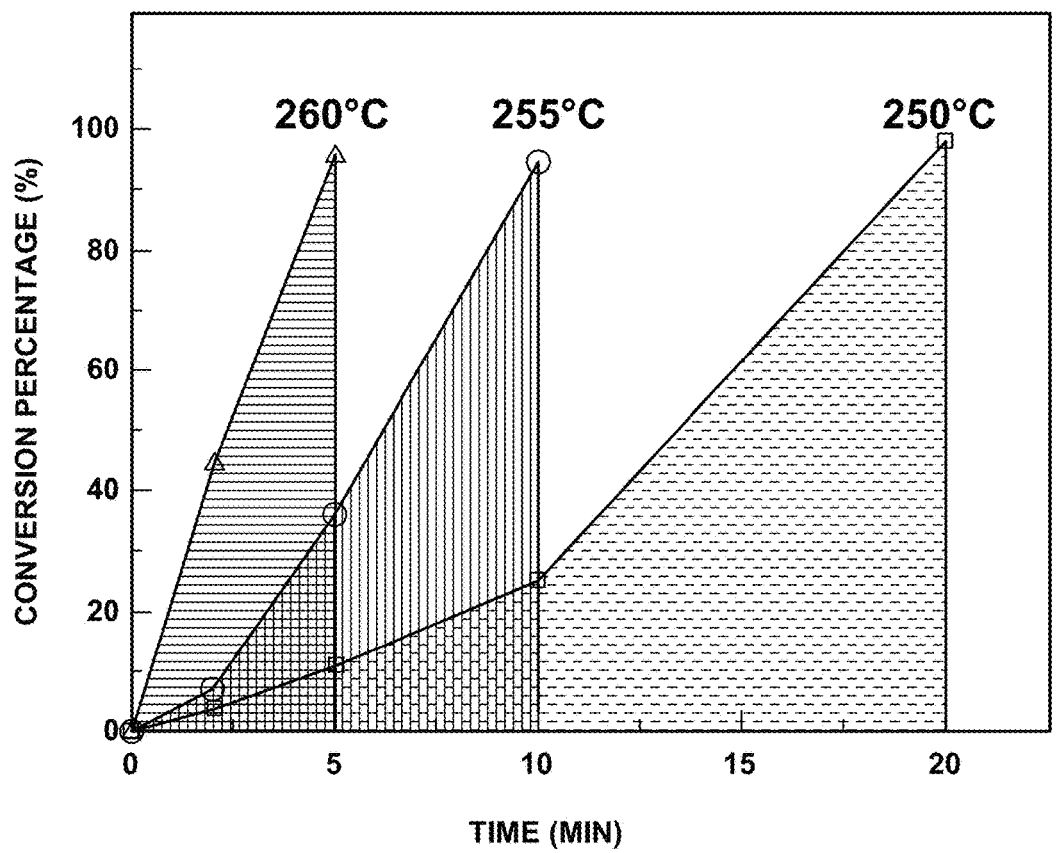
FIG. 2B: Conversion percentage of AJNDE16 to activated state AJNDE16a as a function of exposure time and temperature.

To investigate the response of the molecular probe in the temperature window, reaction kinetics was studied at temperatures of 250° C., 255° C., and 260° C. Since AJNDE16 and AJNDE16a show very different UV absorption spectra, the thermally treated samples of AJNDE16, after a particular period of time, were dissolved in THF to quantitatively monitor the progress of the reaction. As shown in FIG. 2A, when treated at 250° C. for 2 min, AJNDE16 did not show any change. When the sample was isothermally treated at a longer time, for example, 5 min and 10 min, the peak around 433 nm gradually increased, which is consistent with thermal generation of AJNDE16a. After isothermal treatment of the sample at 250° C. for 20 min, most of AJNDE16 has been converted to AJNDE16a. Furthermore, at the higher temperatures of 255° C. and 260° C., the conversion of AJNDE16 to AJNDE16a can be accelerated significantly (FIG. 2B). This study clearly showed that the probe can meet the required operational temperature window.

3.2 Properties of Thermal Damage Probes in Epoxy Resin

Figure 3A:
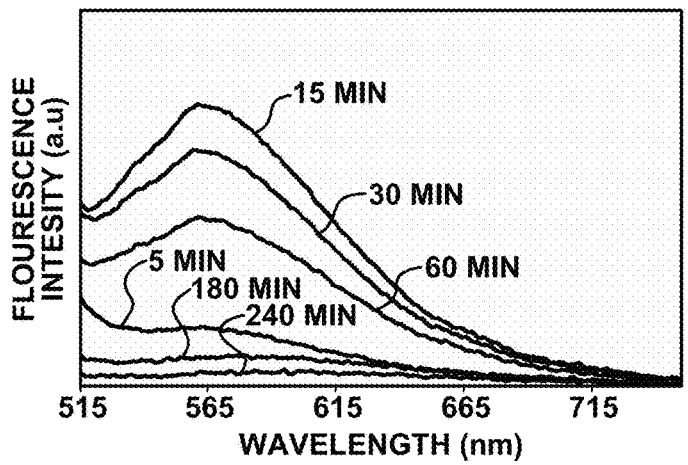
FIGS. 3A-3C. Fluorescence spectrum as a function of exposure time of the probe doped epoxy samples heat-treated at (3A) 204° C.; (3B); 232° C.; and (3C) 260° C.
Figure 3B:
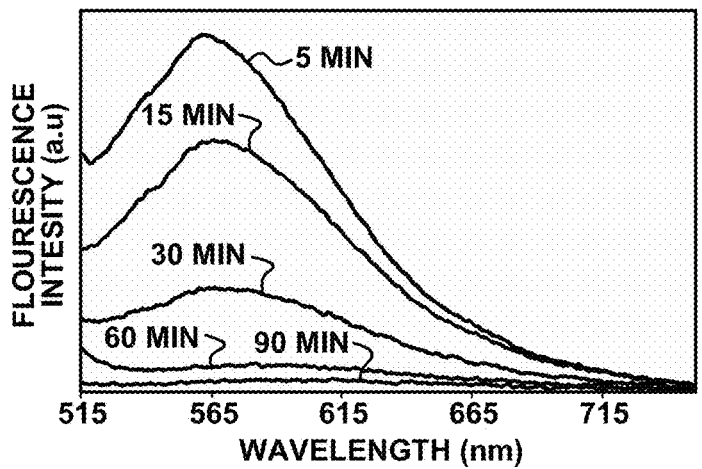
Figure 3C:
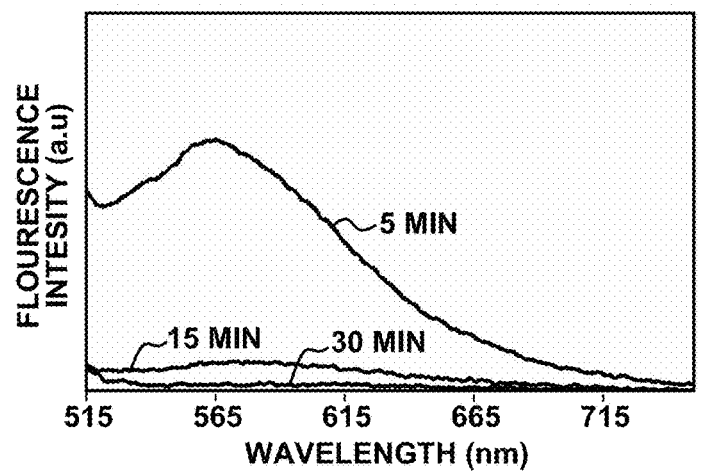

The results of the fluorescence measurements on the films of the probe doped epoxy with the different thermal treatments are shown in FIGS. 3A-3C. The neat epoxy exhibited no fluorescence emission when excited at 470 nm under any of the thermal treatments so no spectra for the neat epoxy are presented. In addition, the as-cured sample of the probe doped epoxy also displayed no fluorescence and was not included in the spectra presented.

The samples treated at 232° C. and 260° C. exhibited maximum fluorescence intensity after 5 minutes of exposure time. However, in the case of thermal treatment at 204° C., it can be seen that the dye reached maximum intensity after 15 min, indicating that the kinetics of activation AJNDE16 were slower at the lower temperature. It should be noted from the kinetics study on AJNDE16, however, that the activation of the probe in the epoxy samples occurred considerably faster than expected at 204 and 232° C. The cause of this change in kinetics in the matrix is still under investigation. It can also be seen that after prolonged exposure to all of the heat-treatment temperatures, the intensity of the fluorescence emission decreased to a level where it could no longer be observed. At the same time, the wavelength of maximum intensity $\lambda_{max}$ also exhibits a bathochromic shift. These phenomena have also been observed in CFRP when using LIF. The rate at which these changes to the fluorescence spectrum occurred was also strongly dependent on the heat-treatment temperature. At 260° C. the fluorescence was no longer observed after 30 minutes, while it took 240 min for the same thing to occur at 204° C. Even though the fluorescence emission becomes harder to see with long exposure times to the point where it cannot be observed visually, this result may not be detrimental to this inspection method. Most thermally damaged parts have a thermal damage gradient surrounding the damage site where the fluorescence may still be visible. In that case, the quenched fluorescence emission can actually be very useful because it indicates an area where severe thermal damage has occurred.

Figure 4A:
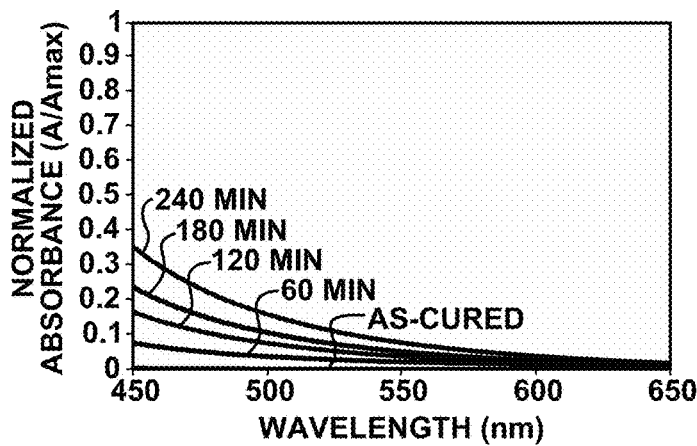
FIGS. 4A-4C. UV-VIS absorption spectra as a function of exposure time for heat-treatments at (4A) 204° C.; (4B) 232° C.; and (4C) 260° C.
Figure 4B:
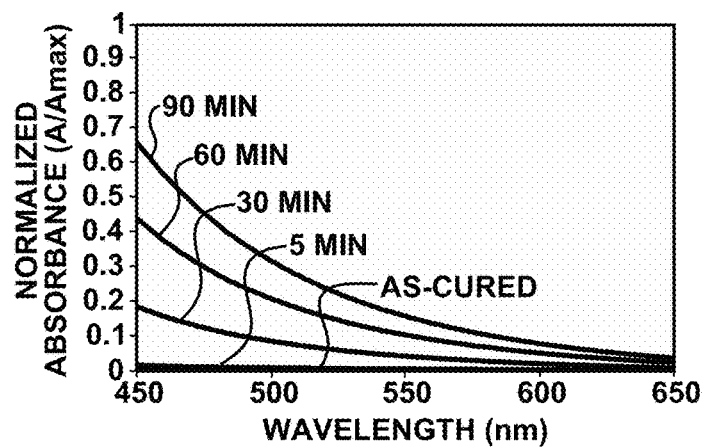
Figure 4C:
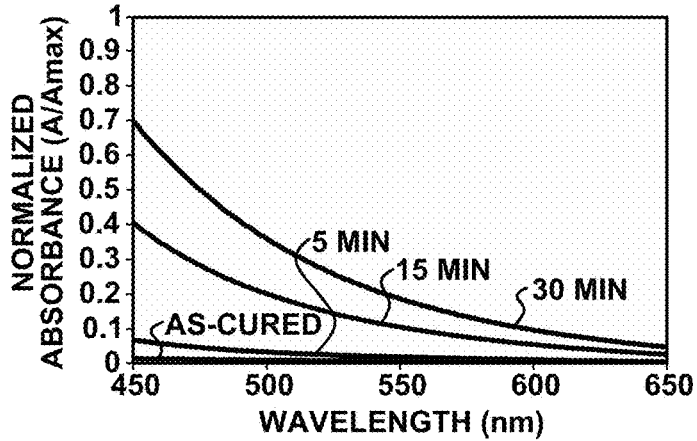

A potential explanation for the change in the fluorescence emission intensity and wavelength as a function of exposure time and temperature can be found by examining the UV-VIS absorption spectra seen in FIGS. 4A-4C. The absorbance of each spectrum was normalized relative to its maximum absorbance $A_{max}$ to account for small variations in the thickness of the films. The absorbance of the thin-films of the probe doped epoxy was too high for the detector to record any values at wavelengths in the UV-range so those spectra could not be normalized. It was found during testing that the decay of the absorption at wavelengths below the maximum absorbance was found to be almost identical to that of the neat epoxy exposed to the same heat-treatment so it is possible to analyze the behavior of the probe doped epoxy in the wavelength range of interest using the UV-Vis spectra from the neat epoxy.

From FIGS. 4A-4C it can be seen that for all three of the heat-treatment temperatures that the absorption between 450 to 650 nm increased as exposure time increased. Looking at the absorption values at 470 nm (excitation source peak) the absorbance increases strongly with increasing exposure time. For example at 260° C. the absorption increases after 15 and 30 min to more than 5 and 10 times respectively the absorbance after 5 min exposure. This means that a significantly less amount of the excitation light is able to penetrate through the epoxy matrix and excite the dye. In addition, the absorbance at 560 nm (the fluorescence peak) is increasing over this period, which means that the fluorescence is likely being absorbed by the matrix as well. The increase in absorbance of the matrix can be attributed to the formation of chromophores during the decomposition process. In similar epoxy-amine cured systems this darkening has attributed to the formation of highly conjugated structures as products of the thermal oxidation of the epoxy.

Figure 5:
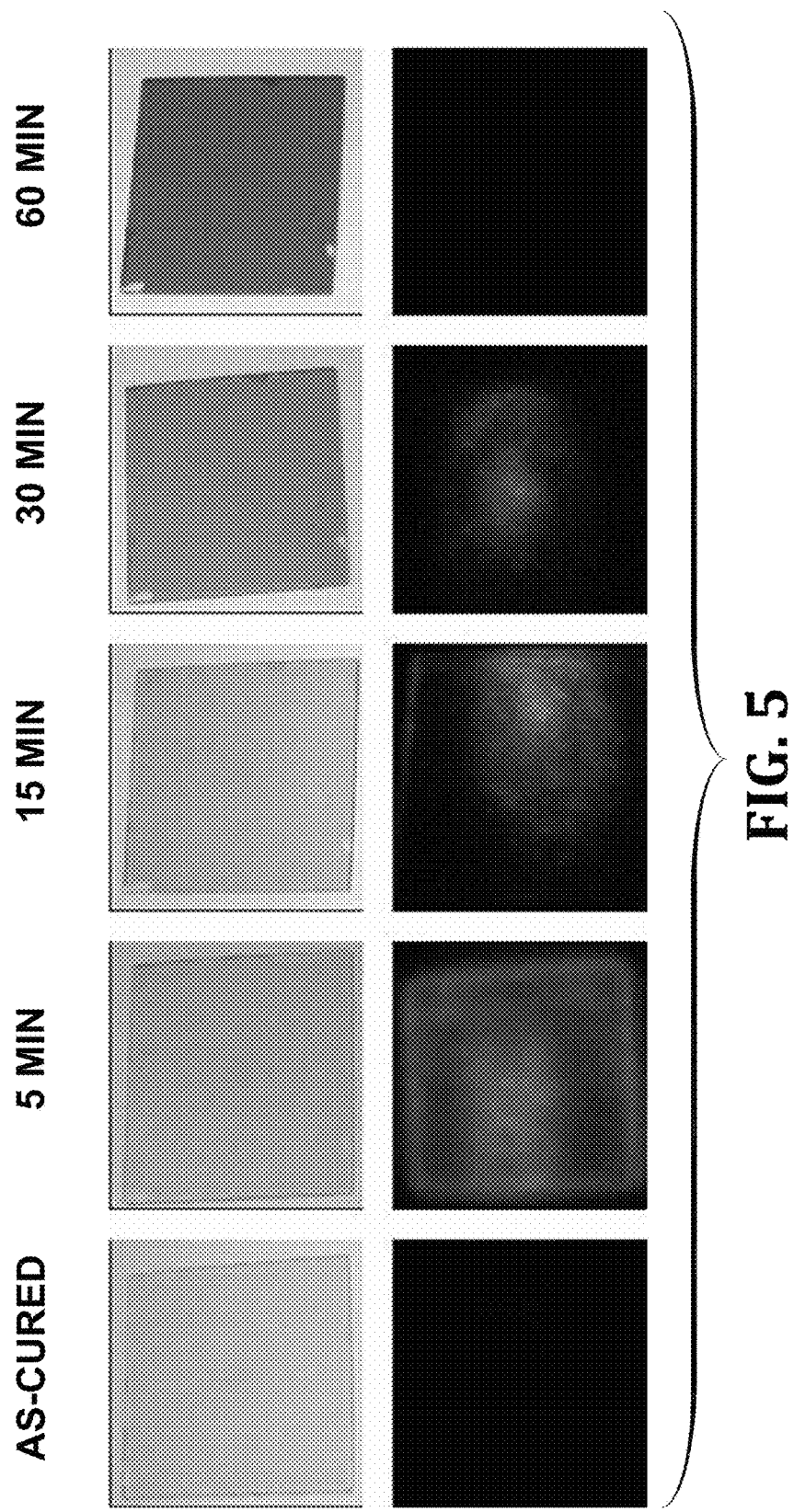
FIG. 5. Bright field (top) and fluorescence (bottom) images of probe doped epoxy thin films heat-treated at 232° C. for several exposure times.

Bright field and fluorescence emission images showing the effects of exposure time on the fluorescence and the darkening (increasing absorbance) of the matrix several exposure times at 232° C. are shown in FIG. 5. A long-pass colored glass filter was used to block out most of the reflected blue light from the excitation source in order to obtain a clearer picture of the fluorescence.

Figure 6:
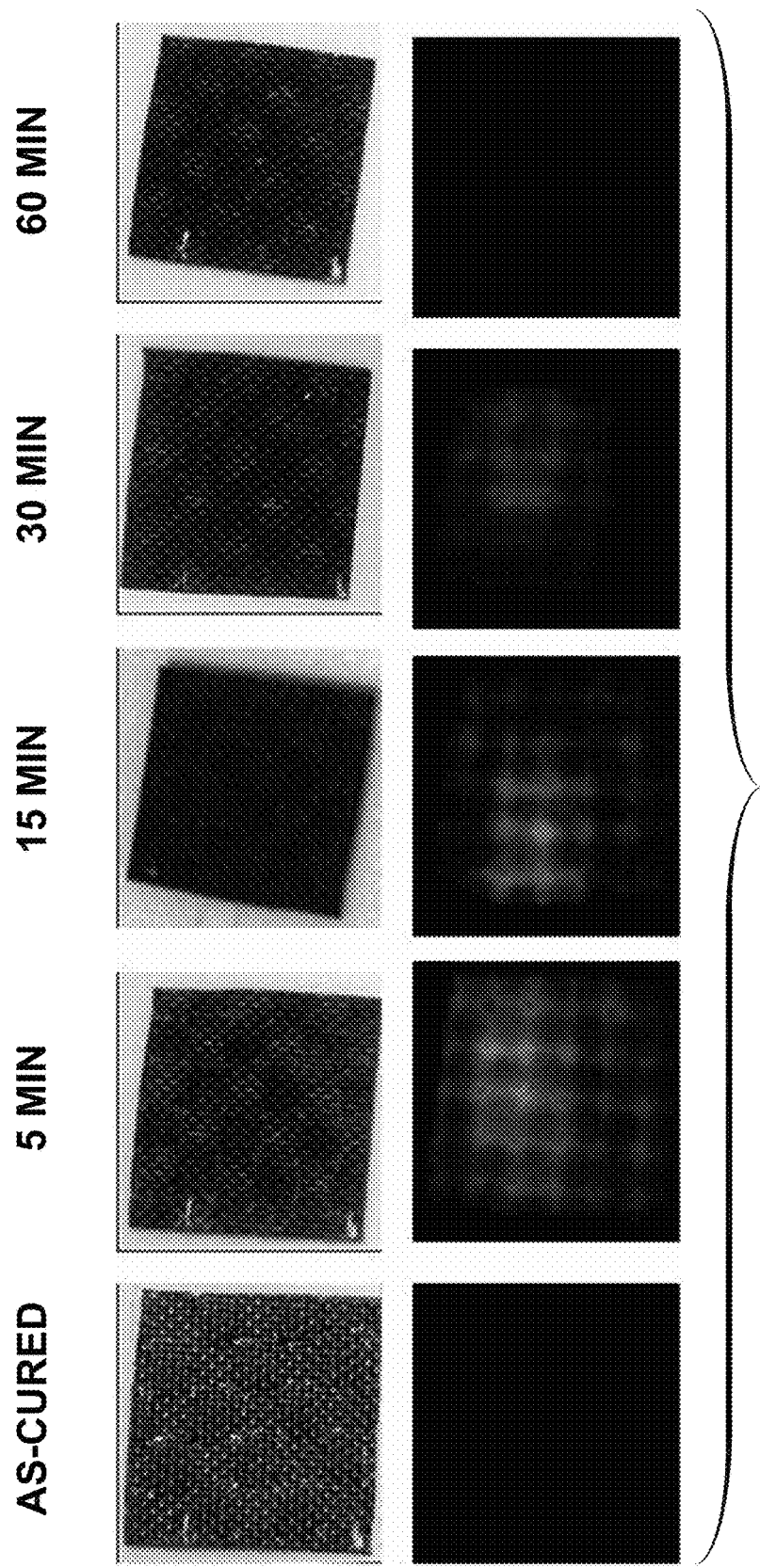
FIG. 6. Bright field (top) and fluorescence (bottom) images of composite with the probe doped epoxy matrix heat treated at 232° C. for different exposure times.

Composites samples with the probe doped epoxy as the matrix were also fabricated and subjected to the same heat-treatments as the resin samples. It was not possible to obtain good fluorescence spectra for the composite samples with the probe doped epoxy as the matrix because the carbon fibers caused significant reflection of the excitation light that saturated the detector and interfered with the spectra of the dye. It is believed that by introducing a filter into the system to block out the reflected light that a fluorescence spectrum similar to that seen for the probe doped epoxy resin will be obtained. While spectra could not be obtained, images of the fluorescence behavior of the composites were taken as shown for the heat-treatment at 232° C. in FIG. 6. A long-pass colored glass filter on the camera lens was used to block out the blue reflected light for these images in order to get a clear view of the fluorescence.

Compared to the resin samples where the thermal degradation was visible to the darkening of the matrix, the thermal degradation is difficult to observe to in the bright field images due to the presence of the carbon fibers. However, the fluorescence behavior can be clearly seen and behaves similar to that seen in the resin samples, indicating that the AJNDE16 is compatible with the composite system.

4. Conclusions

AJNDE16, a thermal damage probe, was incorporated into an epoxy matrix as a means of creating an easily visible inspection method for thermal damage locations to the matrix. Heat-treatment of thin-films of epoxy doped with AJNDE16 revealed that the dye would activate within 5 to 15 minutes in the temperature range of interest and was strongly fluorescent under excitation at 470 nm. With prolonged exposure to thermal treatments the fluorescence intensity decreases and $\lambda_{max}$ experiences a bathochromic shift, which may be useful in identifying areas where significant thermal damage occurred. Changes in the absorbance of the matrix found from UV-Vis spectra may account for the changing of the fluorescence behavior with prolonged exposure. AJNDE16 doped epoxy was also incorporated into a carbon fiber composite using wet lay-up. No fluorescence spectra were obtained for the probe doped epoxy combined with carbon fibers due to strong scattering of the excitation light by the carbon fibers. However, images of the fluorescence were obtained and seem to indicate that the fluorescence behavior of the composite specimens doped with AJNDE16 is similar to that seen in the resin samples.

Example 2. Time-Temperature Indicator for Evaluating Incipient Thermal Damage Incipient thermal damage is a significant issue for CFRP composites because it is difficult to detect by common NDE techniques like ultrasound and it can cause fiber-matrix debonding, delamination, and matrix embrittlement which can reduce the mechanical properties of the composite. Diffuse reflectance infrared transform spectroscopy (DRIFTS) is capable of detecting incipient damage, but it has a small spot size that is not efficient for inspecting large areas for thermal damage. In our previous work a thermally activated fluorescent probe was shown to activate when the composite was thermally exposed. This "turn-on" type behavior could show that thermal exposure had occurred, but could not provide more details about the thermal event. In this study a method for estimating the time and temperature of the thermal exposure (a so-called time-temperature indicator or TTI) is presented. The basis for this method is combining two different thermally activated probes with different activation kinetics and emission wavelengths. Using ratiometric fluorescence to monitor the changes in the fluorescence spectra, time-temperature response curves can be generated that can be used for estimating the time and temperature of the thermal exposure.

1. Introduction

The increased use of carbon-fiber reinforced plastic (CFRP) composites as structural components in aircraft has led to the need to develop nondestructive evaluation methods that can detect damage mechanisms that are distinct to composite structures. An area of recent interest is the detection of the onset of thermal damage commonly termed incipient thermal damage (ITD). Incipient thermal damage of CFRP can reduce mechanical properties such as flexural strength, compression after impact (CAI) and interlaminar shear strength (ILSS), and it is not reliably detected by visual inspection or ultrasound techniques. Characterization techniques such as Fourier transform infrared spectroscopy (FTIR), laser-induced fluorescence (LIF) of the epoxy matrix, Raman spectroscopy, and nuclear magnetic resonance (NMR) have all been used to detect and evaluate incipient thermal damage of composites. These detection methods have been shown to be capable of finding incipient thermal damage in laboratory tests, but the suitability of many of these techniques to the inspection of in service parts may be limited. With the development of handheld FTIR units, diffuse reflectance infrared Fourier transform (DRIFT) spectroscopy is currently the most feasible technique for field inspections. While the handheld FTIR units are sensitive enough to detect incipient thermal damage, they have a small spot size relative to the parts being inspected so it is not suitable for wide-area inspection. Thus if the thermal damage site is not already well defined, it can be a challenge to properly inspect the damage.

FIG. 1A depicts the mechanism of how the thermal damage probes work, as discussed above in Example 1.

While activation of the thermal damage probe could indicate that a significant thermal event occurred it was not reliable for determining the extent of the thermal damage. This is because the measurement of the activated probe only exhibited a change in fluorescence intensity which is difficult to reliably measure. However, it was found that when the fluorescence of the probe was combined with the autofluorescence of the epoxy matrix that the fluorescence emission shifted depending on the time and temperature of the thermal exposure. This led to the development of a multiplexed thermal damage probe system described in this Example, where two thermal damage probes are combined in a single matrix.

A time-temperature indicator (TTI) gives a record of the cumulative time-temperature history of the object of interest. The vast majority of TTI literature is focused on the food packaging industry and as a way to monitor the shelf life of packaged food subjected to temperature abuse, although TTI have potential in many other industries where products are subject to degradation by temperature abuse. TTI useable up to 200° C. were found in the literature, but since the ITD of the CFRP studied can occur at temperatures well over 200° C. they were not usable for this application.

In this Example a TTI for estimating thermal exposure in the range of ITD using a multiplexed system of fluorescent thermal damage probes is detailed. First the kinetics of the activation of two thermal damage probes known as AJNDE16 (FIG. 1B) and AJNDE35 (FIG. 1C) are characterized and a kinetic model for both probes is developed. This is followed by characterization of the response of the multiplexed system to thermal exposure and the generation of a model to predict the multiplexed system fluorescent emission. Lastly the methodology for utilizing the multiplexed system as a TTI for ITD is demonstrated.

2. Experimentation

2.1 Probe-Doped Epoxy Preparation

2.1.1 AJNDE16-Doped Epoxy

Thermal damage probe AJNDE16 was mixed into Hysol EA 9390 part A (Henkel), a tetraglycidal-4-4'-diaminophenylmethane (TGDDM) base resin. The AJNDE16-doped resin was then combined with curing agent 2,2'-Dimethyl-4,4'-methylenebis(cyclohexylamine) (MMCA) in a weight ratio of 1:0.56. The amount of AJNDE16 in the final mixture was 0.05 wt %. The AJNDE16-doped epoxy was cured at 121° C. for 150 min.

2.1.2 AJNDE35-Doped Epoxy

Thermal damage probe AJNDE35 had a tendency to form aggregates that were difficult to disperse in the TGDDM resin so it first dissolved in methyl ethyl ketone (MEK) in a ratio of 10 mg AJNDE35:1 g MEK. The MEK mixture was then mixed into the TGDDM resin and left in a fume hood until the MEK evaporated out of the resin (~1 day). AJNDE35-doped resin was then mixed with MMCA and cured at 121° C. for 150 min. The amount of AJNDE35 in the final mixture was ~0.05 wt %.

2.1.3 Multiplexed Epoxy

To prepare the multiplexed samples both probes AJNDE16 and AJNDE35 were dispersed in MEK using a ratio of 10 mg probe:1 g MEK. Solutions for both probes were mixed into the same TGDDM resin and then left until the MEK had evaporated. The resin containing both probes was then mixed with MMCA and cured at 121° C. for 150 min. The probes were combined in approximately a 1:1 molar ratio which corresponded to 0.05 wt % AJNDE16 and 0.054 wt % AJNDE35 in the sample.

The multiplexed epoxy was also coated on a 8-ply 30.5 cm×30.5 cm, 8 ply composite panel with a polyester peel ply (Precision Fabrics 60001). The coating was then cured at 121° C. for 150 min. After curing the panel was cut into 7.62 cm×7.62 cm specimens.

2.1.4 Kinetic Measurement Sample Preparation

The kinetic measurements required that the samples not become oxidized during thermal exposure because oxidation of the matrix was previously found to quench the fluorescence emission of the probes. In order to fabricate samples that wouldn't oxidize small drops of the AJNDE16-doped epoxy, AJNDE35-doped epoxy, and multiplexed epoxy samples were sandwiched between a glass slide and a cover slip with cover slips placed at the ends of the glass slide to act as a spacer. The samples were then processed using a conventional vacuum bagging process. The samples were cured at 121° C. for 150 min while the system was under vacuum.

2.2 Fluorescence Measurements

Fluorescence measurements were made on a Stellarnet BlueWave UVN spectrometer with a R600-8-UVVIS SR reflectance probe. The probe contains a 600 μm read fiber (detector) at the core and is surrounded by 7 fibers that focus the excitation source onto the sample. A 470 nm LED with a 472 nm bandpass filter (Edmund Optics) was used as the excitation source for the AJNDE16-doped epoxy measurements. For AJNDE35-doped epoxy and multiplexed epoxy a 430 nm LED with a 435 nm bandpass filter (Edmund Optics) was used as the excitation source. The spot size of the excitation light was approximately 2-3 mm. The integration time for the detector was set to 10,000 ms and 3 scans of each spectrum were averaged.

2.2.1 Kinetic Measurements

To determine the activation kinetic of probes AJNDE16 and AJNDE35 fluorescence intensity measurements were utilized. Fluorescence intensity measurements are difficult to reproduce unless done under strict experimental conditions so a specialized testing procedure was developed in order to obtain acceptable results for the kinetics measurements. In order to achieve good results the exact same location on the sample had to be excited and measured every time. To do this an in-house fixture was fabricated to hold the sample and the position of the spectrometer and fixture were held constant throughout the measurement.

To perform the measurements the sample was first thermally exposed at a temperature of interest for a discrete amount of time (15 min to 2 hrs). After the thermal exposure the sample was removed from the oven and a fluorescence measurement was taken using the spectrometer. The sample had to be cooled to room temperature before measurement to avoid thermal quenching caused by the increase in efficiency of non-radiative decay processes at higher temperatures. To verify the measurement was reproducible, the sample was removed from the fixture and replaced and another spectrum was recorded. This process was repeated at least three times. If the difference in the intensities was on the order of the noise in the measurements, the measurements were considered satisfactory and the average of the measurements was taken. The same sample was then placed back into the oven at the same temperature and this process was repeated until the change in the intensity between measurements was on the order of the noise of the spectrometer.

2.3 Localized Heating of CFRP Panel with Multiplexed Coating

Localized heating experiments were performed on the CFRP panels with the multiplexed coating. Two silicone heat blankets (Omega Engineering) were placed on separate sides of the panel. A 7.62 cm circular heat blanket was placed on the uncoated side of the panel and a 2.54 cm square heat blanket was placed on the side with the multiplexed coating. The 7.62 cm blanket was used to warm the whole panel up to reduce the heat flow through the composite panel from the locally heated area and increase the size of the thermal gradient outside of the area locally heated by the 2.54 cm square blanket on the coating side. Six thermocouples aligned in a line and spaced approximately 5 mm apart were used to monitor the temperature in and just outside of the locally heated area on the coating side of the panel. Two more thermocouples were placed on the backside of the panel to monitor the temperature during heating using the 7.62 cm blanket. The entire setup was then sandwich between two insulating blocks and wrapped in an insulating cloth to reduce heat loss.

3. Results and Discussion

3.1 Thermal Damage Probe Kinetics

From the mechanism depicted in FIG. 1, it is expected that the thermal damage probes would exhibit an irreversible unimolecular decomposition reaction upon exposure to sufficient heat. The traditional rate equations for unimolecular decompositions could not be applied in this case because the concentration of the probe illuminated by the excitation source was not known. Instead a phenomenological analog was developed where the probe was assumed to be in one of two states called $\alpha$ and $\beta$. $\alpha$ represents the fraction of measurable probe in the off state (probe before thermal exposure) and $\beta$ is the fraction of measurable probe in the on state (fluorescent product after thermal exposure). Thus the relationship between $\alpha$ and $\beta$ is defined in Equation 1.

$$\alpha + \beta = 1 \qquad [1]$$

Since β represents the fraction of the probe in the on state, it is the quantity that is found from the fluorescence intensity measurements after thermal exposure. The definition of β in terms of the intensity measurements is given in Equation 2.

$$\beta = I/I_\infty \quad [2]$$

Where I is the measured intensity and $I_\infty$ is the measured intensity at t=infinity when all the measureable probe has been activated. Using these definitions to modify the traditional rate equation for a unimolecular decomposition reaction, the phenomenological rate equation can be defined as shown in Equation 3.

$$r = d\alpha/dt = k\alpha^n = k(1-\beta)^n \quad [3]$$

Where $d\alpha/dt$ is the rate of change of α, k is the rate constant, and n is the order the reaction.

3.1.1 Kinetic Measurements of Thermal Damage Probes

An example of the fluorescence intensity measurements for an AJNDE35-doped TGDDM-MMCA samples thermally exposed at 204° C. for various times can be seen in FIG. 3a. The spectra in FIG. 3a are normalized by $I_\infty$. FIG. 3b and FIG. 3c display the plots of a versus time for probes AJNDE16 and AJNDE35 respectively. It should be noted that for the AJNDE35 kinetic measurements $I_\infty$ was not measured directly due to the significant amount of time necessary for the process to go to completion. Instead $I_\infty$ was extrapolated by fitting a function to the difference in intensities between each time increment and then using that function to predict when the changes between time increments would be on the order of the noise in the measurements.

Figure 7A:
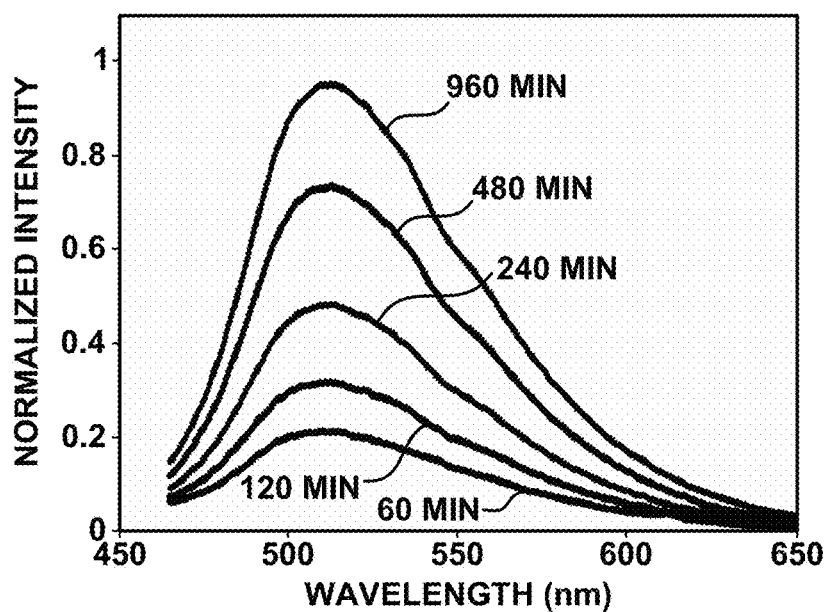
FIGS. 7A-7C. (7A) An example of fluorescence intensity spectra for AJNDE35 at 204° C.; (7B) a versus time for AJNDE16; and (7C) a versus time for AJNDE35.
Figure 7B:
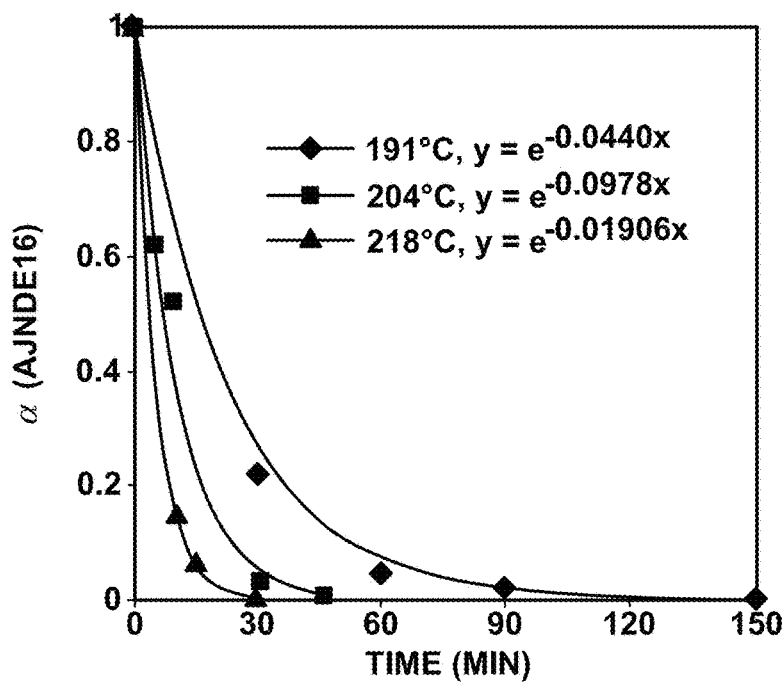
Figure 7C:
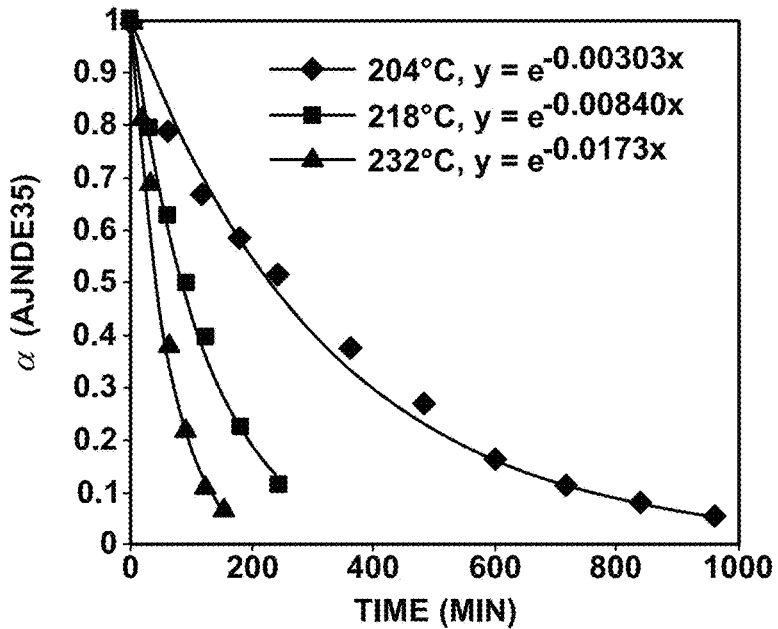

As illustrated in FIGS. 7A-7C, all the plots for α as a function of time are best fit by exponential functions, which is indicative of a first order reaction rate. Integrating the rate law in Equation 3 with order n=1 the expression for a takes on the form in Equation 4.

$$\alpha = \alpha_0 \exp(-kt) \quad [4]$$

Where $\alpha_0$ is the initial value of α, k is the rate constant, and t is time. No fluorescence from the activated probes was observed in as-cured spectra so $\alpha_0$ was assumed to be equal to 1 at t=0. Comparing the results in FIG. 3b and FIG. 3c it can be seen that the decomposition of AJNDE35 occurs at a much slower rate than AJNDE16 at the same temperature.

3.1.2 Apparent Activation Energies of Thermal Damage Probes

The rate constant is a function of the activation energy and temperature as shown in Equation 5.

$$k = Z\exp(-E_A/RT) \quad [5]$$

Where Z is a preexponential factor, $E_A$ is the activation energy, R is the universal gas constant, and T is the temperature in Kelvin. Since the kinetic measurements are based on phenomenological results the activation energy obtained from these results is not necessarily the actual activation energy and it is more aptly described as the apparent activation energy. The activation energy and preexponential factor can be determined using an Arrhenius plot. The Arrhenius plot for AJNDE16 and AJNDE35 is shown in FIG. 8.

Figure 8:
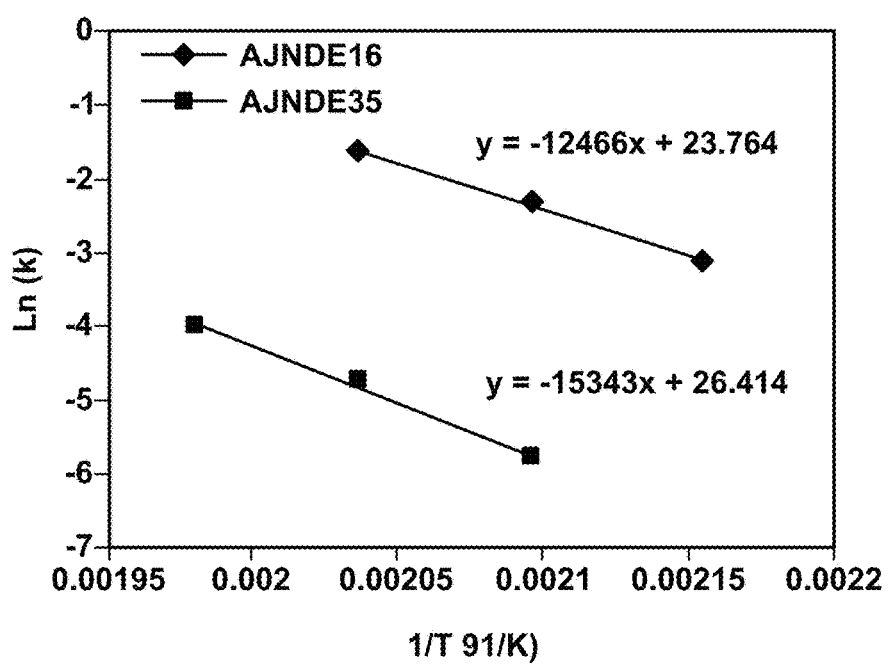
FIG. 8. Arrhenius plot for AJNDE16 and AJNDE35.

From FIG. 8 it can be seen that the plots for both AJNDE16 and AJNDE35 are fit well by linear equations verifying the Arrhenius relationship. The apparent activation energy and preexponential factors for both AJNDE16 and AJNDE35 are presented in Table 1.

TABLE 1

Apparent activation energy and preexponential factor for probes AJNDE16 and AJNDE35.

| Probe | Apparent $E_A$ (kJ/mol) | Z ($s^{-1}$) |
|---|---|---|
| AJNDE16 | 104 | $2.09(10^{10})$ |
| AJNDE35 | 128 | $2.96(10^{11})$ |

3.1.3 Kinetic Modeling of AJNDE16 and AJNDE35 Fluorescence

The first step in establishing a model for AJNDE16 and AJNDE35 was to find functions that could accurately describe the peak shape. Five peak functions were evaluated as potential fits for the fluorescence peaks of AJNDE16 and AJNDE35 using Igor Pro 6 software (Wavemetrics). Those peak functions were Gaussian, Lorentzian, Voigt, lognormal, and exponentially modified Gaussian models. The best peak fit was determined by finding the minimum of the sum of squared residuals (SSR) between the measured spectra and the model function. It was found that best fit for both probes was an exponentially modified Gaussian function. To verify that the peak shape was not changing significantly during activation, peak fitting was performed on five peaks with different exposure time and/or temperature. Little variation was found in the peak fitting parameters indicating the peak shapes for both probes were constant throughout the activation process. Since only the intensity changes during activation, the kinetic model for the fluorescence of the probe can be described by Equation 6.

$$P = \beta_i P_i \quad [6]$$

Where P is the peak at a given level of activation (β) for probe "i" (i.e., AJNDE16 or AJNDE35), is the fraction of probe "i" that has been activated as described by Equation 2, and $P_i$ is the peak fit function for probe $\beta_i$ for the model was found by first calculating $\alpha_i$ using Equation 4 for the probe and then solving the relation in Equation 1 for β. The rate constant k was determined using Equation 5 and the apparent activation energy and preexponential factor found in Table 1. A comparison of the model predictions and the experimental results for probes AJNDE16 at 191° C. and AJNDE35 at 204° C. is shown in FIGS. 9A and 9B.

Figure 9A:
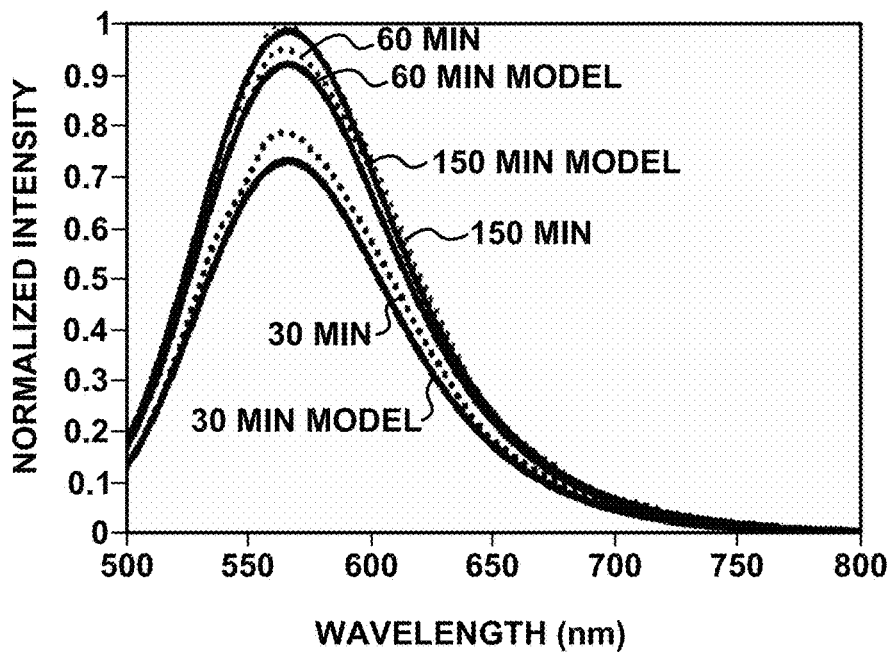
FIGS. 9A and 9B. Comparison of kinetic model to experimental data for (9A) AJNDE16 at 191° C.; and (9B) AJNDE35 at 204° C.
Figure 9B:
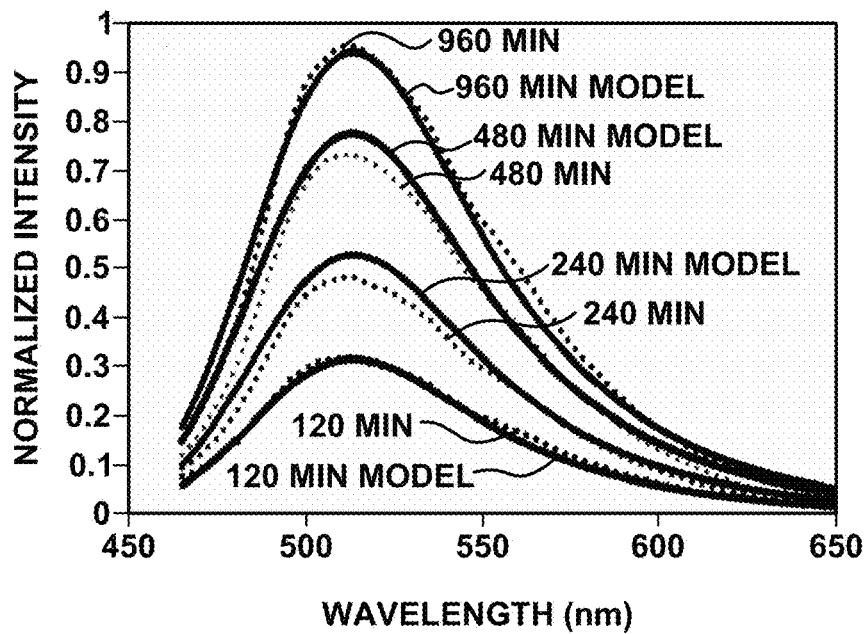

From FIGS. 9A and 9B it can be seen that for both AJNDE16 and AJNDE35 the model matches well with the experimental data for the most part. The relative error was always found to be less than 10% which is reasonable when taking into account the experimental error in the measurement. These results show that the model in Equation 6 can be expected to reasonably predict the kinetics of activation for both probes at a desired temperature.

Figure 10:
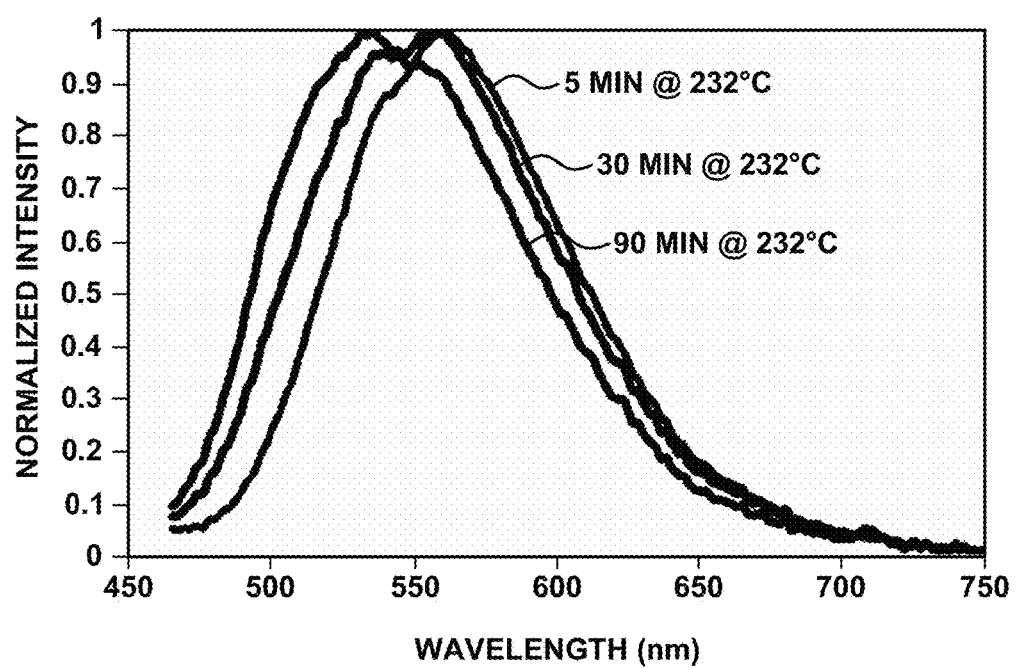
FIG. 10. Multiplexed sample of AJNDE16 and AJNDE35 in TGDDM-MMCA.

3.2 Multiplexed Thermal Damage Probe System
3.2.1 Fluorescence Response of Multilplexed System Fluorescence spectra of the multiplexed system containing both probes AJNDE16 and AJNDE35 exposed at 232° C. for several exposure times is shown in FIG. 10. The spectra were normalized by the maximum intensity of the individual spectrum to give a better view of the changes in the peak shape. Fluorescence images of the sample at different exposure times are shown in the bottom of FIG. 10. The excitation light for the images was a white light source with a 435 nm bandpass filter.

From FIG. 10 it can be seen that after the short 5 minute exposure, the peak maximum is found around 563 nm. The peak from the 5 minute exposure is very close to the peak observed from AJNDE16 by itself. From the kinetics measurements it is known that AJNDE16 will activate much quicker than AJNDE35 so it is expected that for a short exposure the AJNDE16 peak would be dominate. As the exposure time increases a shoulder around 535-540 nm starts to grow and eventually becomes the peak maximum. Again this result is expected because the peak for AJNDE35 appears around 514 nm so as the amount of AJNDE35 activated increased it was expected that it would contribute more to the spectrum and blue-shift the spectra. This spectra shift as function of thermal exposure in the multiplexed system provides a better means to quantify the thermal exposure of the part than a single thermal damage probe where only an intensity change would be observed.

The fluorescence images at the bottom of FIG. 10 display a similar trend to the spectra. Initially the sample exhibits a weak muddy orange fluorescence, but as the exposure time increases the fluorescence begins to turn green and after 90 minutes at 232° C. it is bright green.

3.2.2 Modeling of Multiplexed System

It is expected that the multiplexed probe system can be modeled as the superposition of the fluorescence of probes AJNDE16 and AJNDE35. Thus the equation for such a multiplex model can be defined as shown in Equation 7.

$$P_m = \beta_{16} P_{16} + r \beta_{35} P_{35} \qquad [7]$$

Where $P_m$ is multiplexed system spectra, r is a weighting factor, and the $\beta_{16} P_{16}$ and $\beta_{35} P_{35}$ terms are the kinetic models for AJNDE16 and AJNDE35 respectively from Equation 6. Currently the value of r has been found by minimizing the sum of squared residuals of Equation 7 to the empirical data, but it is believed that it should be possible to find the r value from material properties of the probes and the stoichiometry of two probes in the sample. However, all the factors that affect r have not yet been determined so the value of r must still be determined empirically for now. The r value for the multiplexed system in this study was found to be 1.561. A comparison of the model in Equation 7 to measured spectra of the multiplexed samples heat-treated for various times at 232° C. can be seen in FIGS. 11A and 11B. All spectra were normalized by the maximum intensity of the multiplexed system.

Figure 11A:
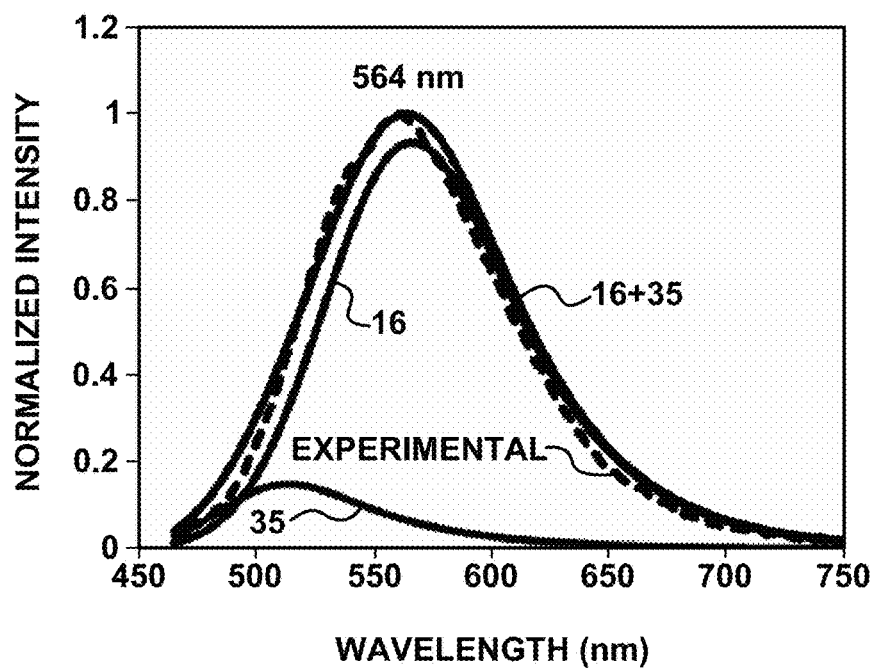
FIGS. 11A and 11B. Comparison of multiplex model to measurements for different exposure times at 232° C. (11A) 5 min; and (11B) 90 min.
Figure 11B:
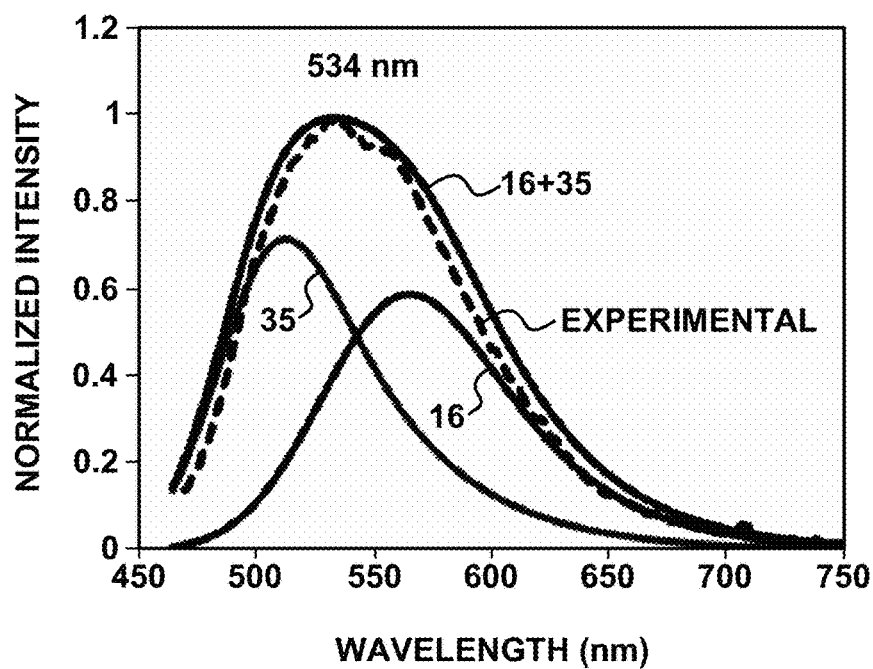

From FIGS. 11A and 11B it can be seen that the model for the multiplexed system in Equation 7 does a relatively good job of fitting the measurements and thus validates that the measured fluorescence spectra is formed by the superposition of the fluorescence peaks from AJNDE16 and AJNDE35. The model fails to capture the shoulder that is observed in the measured spectra, but it tends to captures the maximum of the shoulder. Another interesting note is that according to the kinetic models AJNDE16 is fully activated before AJNDE35 reaches 20% activation meaning that for most of the thermal exposure in the multiplexed system the AJNDE16 peak is essentially an unchanging reference peak.

3.2.3 Ratiometric Fluorescence and Response Curves

Figure 12:
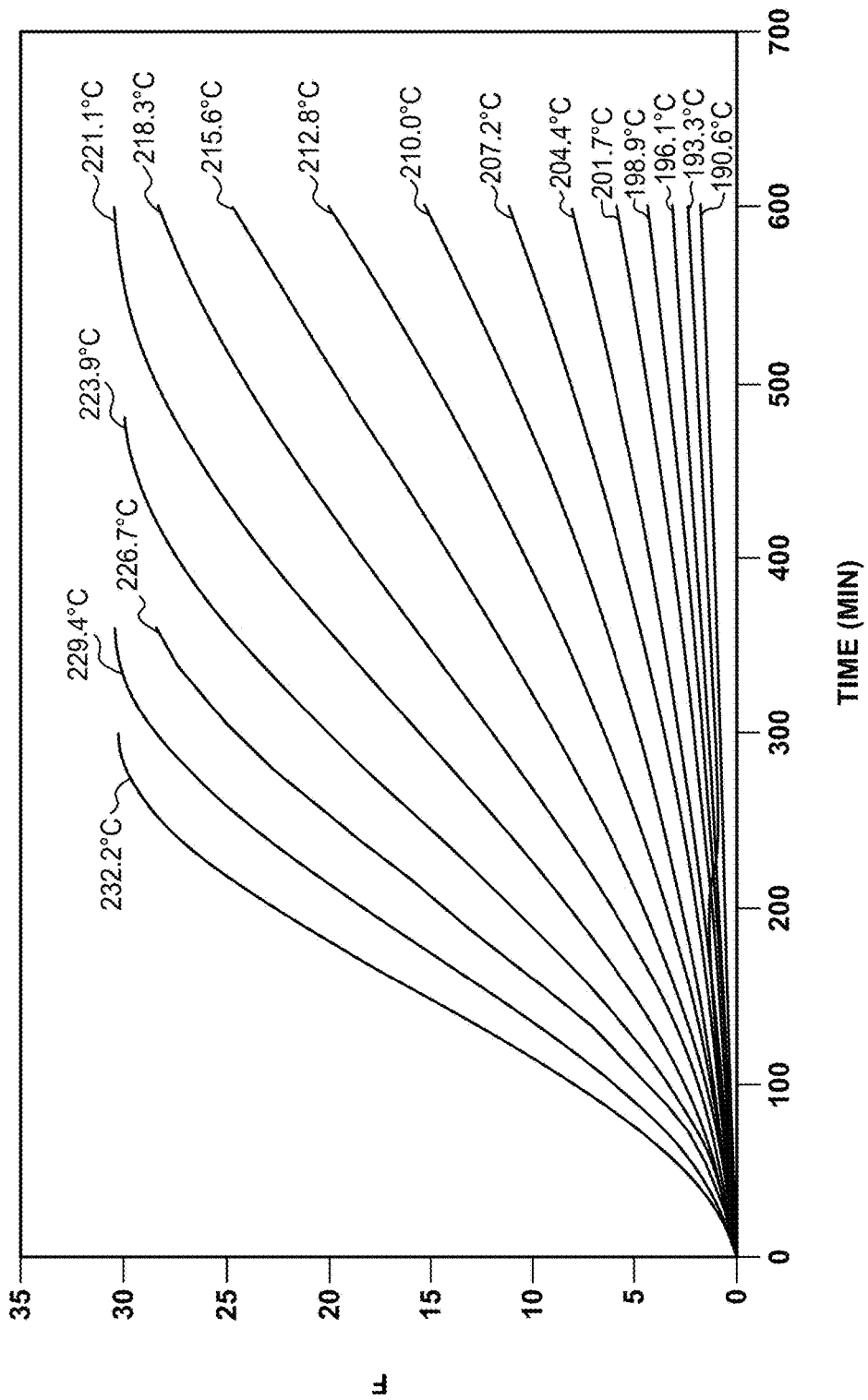
FIG. 12. Response curves for thermal exposure for temperatures ranging from 190.6° C. to 232.2° C.

The multiplexed system of thermal damage probes allows for the use of ratiometric fluorescence techniques which provide a more reliable method for quantification than fluorescence intensity measurements. In the literature, ratiometric fluorescence systems often have well separated peaks and thus defining the ratiometric response is usually straightforward as dividing the peak intensity of the two fluorescent species. Thus the initial thought was to use the intensities at 514 nm and 565 nm which correspond to the peaks of the individual probes, but this ratio did not turn out to be very accurate. It is believed that the reason for this is that at 514 nm there may be some noise in the fluorescence peak caused by scattered light from the excitation source being recorded by the detector. Since it is very difficult to control the amount of scattering of the excitation, the intensities in the fluorescence spectrum near the excitation peak tend to vary much more significantly than the intensities at higher wavelengths where there is little or no light from the excitation source. To avoid the wavelengths where the scattered light might affect the intensity, 540 and 560 nm were chosen as the wavelengths to ratio. These wavelengths were selected because they were wavelengths where change is observed in the spectra throughout the thermal exposure. Using this intensity ratio a response function was defined to provide a relationship between the fluorescence measurements and the thermal exposure. The response function was adapted from the literature and is given in Equation 8.

$$F = \frac{(R - R_{min})}{(R_{max} - R)} \qquad [8]$$

Where F is the response function, R is the ratio of intensities at 540 and 560 nm ($I_{540}/I_{560}$), and $R_{min}$ and $R_{max}$ are the minimum and maximum possible value of R. For the defined R, $R_{min}$ was found to be 0.791 and $R_{max}$ was equal to 1.13. Using this response function and the multiplexed system model, response curves for temperatures ranging from 190.6° C. to 232.2° C. (390° F. to 450° F.) were generated with intervals between curves ~2.7-2.8° C. (~5° F.). A plot of the response curves for the temperature range described above can be seen in FIG. 12. It should be noted that the points in the plot are not measurements but discrete F values determined using the multiplexed system model.

All the response curves were generated by fitting the F values generated using the multiplexed system model in Equation 7 with third order polynomials and the $R^2$ values were greater than 0.99. It should be noted the curves were limited to have a maximum value of F less than 30, because when F is greater than 30 the curve begins to plateau as it approaches full activation of both AJNDE16 and AJNDE35 and this causes the quality of the fit to decrease. While this may seem like a limitation of the response curves the time-temperature combinations where F is greater than 30 is usually sufficient to cause enough damage to the composite where ultrasound can start to detect the damage. This means that technically the damage would no longer be considered to be in the ITD range for which the probes are designed; thus showing that the multiplexed system covers the range of ITD for this composite system.

It should also be pointed out that to obtain reasonably good accuracy with the response curves that it is necessary to have increments as small as ~2.7-2.8° C. between curves because the measurements are so sensitive to temperature that if this increment is much larger a significant amount of error can be introduced if the temperature of the exposure falls between two response curves. As an example, assume a value of F equal to 7 was measured and that the temperature range was somewhere between 218.3° C. and 223.9° C. For a value of F equal to 7 the 218.3° C. and 223.9° C. response curves would correspond to correspond to 314 min and 218 min respectively. So a difference of 5.6° C. can change the estimated time for the measurement by almost 100 min.

3.3 Application of Multiplexed System as a TTI for ITD of CFRP

Determining the actual thermal history of the part is difficult because there are many different thermal exposures that can lead to the same spectra. Currently there are two ways that the response curves can be utilized for a TTI system. The first is to define a reference temperature and then use that responsive curve and a measured F value to determine the estimated time at the exposure. A given F value is an equivalent state that is independent of the thermal loading path to reach that state. Thus the estimated time from the response curve would represent the time at defined temperature to reach that state since the actual thermal history is likely unknown. In the second method, a time value is defined (e.g., 1 hour) and the effective temperature is determined. This approach has been taken when classifying samples measured for ITD using FTIR measurement. In either case an equivalent state of thermal exposure is defined and the results can be compared to calibration sets for thermal damage in order to evaluate the how damaged in the part is.

3.3.1 Set Temperature

Figure 13A:
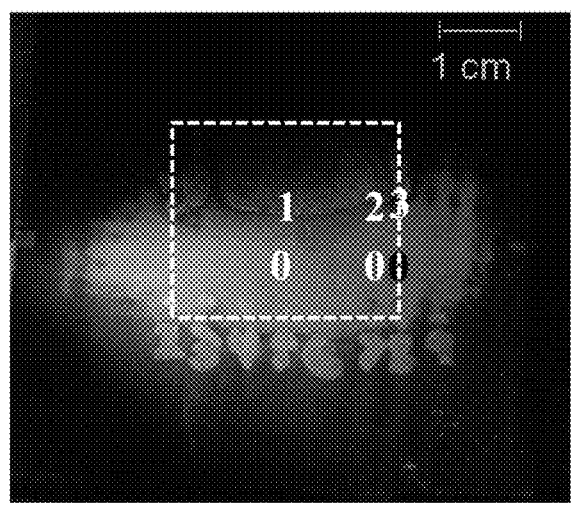
FIGS. 13A-13C. Multiplexed coating sample subjected to localized heating for ~90 min.: (13A) fluorescence image; (13B) thermocouple measurements; and (13c) fluorescence measurements.
Figure 13B:
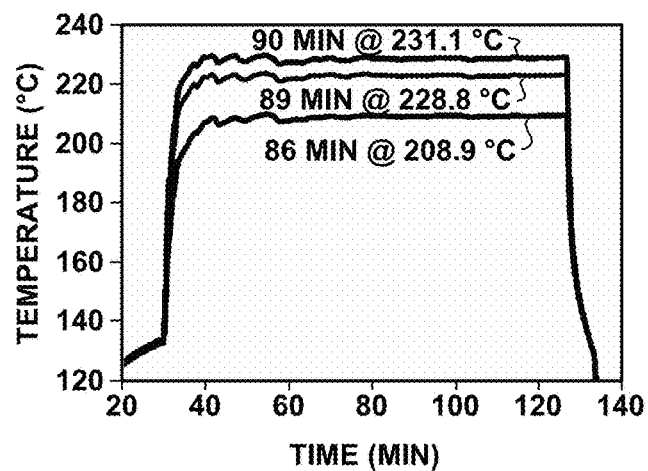
Figure 13C:
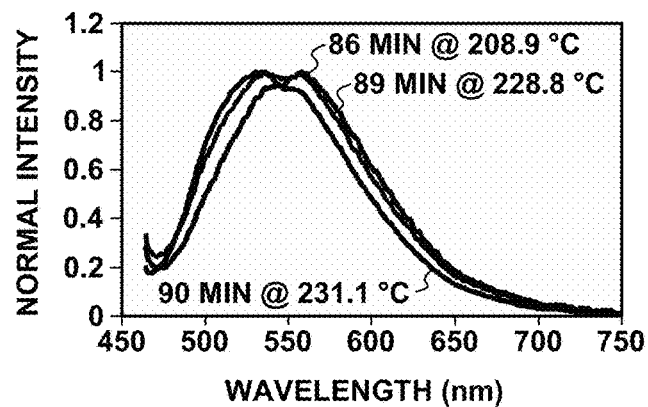

A fluorescence image of the panel coated with the multiplexed system that was locally thermally exposed can be seen in FIG. 13A. The fluorescence image was taken with a white light source with a 435 nm bandpass filter. The dashed box in the figure indicates where the heating blanket was located and the superimposed colored circles represent the locations where thermocouple and fluorescence measurements were taken. The thermocouple data and associated fluorescence spectra can be seen in FIG. 13B and FIG. 13C, respectively.

From the fluorescence image in FIG. 13A, it can be seen that the fluorescence emission varies significantly near the edge of the where the blanket was placed. While not depicted in color in FIG. 13A, outside the fluorescence is the orange characteristic of AJNDE16 and inside the fluorescence is green which is indicative that a significant amount of AJNDE35 has been activated. A yellowish fluorescence can be seen in between the orange and green fluorescence which is likely an intermediate state where both AJNDE16 and AJNDE35 are both contributing significantly to the spectra. Based on knowledge of the kinetics and the temperatures measured with the thermocouples these results were expected. Near the center of the heating blanket the temperature was relatively high (~231° C.) thus it would be expected that both probes would respond. At the edge of the heating blanket the thermal gradient began to appear and the temperature starts to drop rapidly to below 200° C. where only AJNDE16 would be expected to activate enough to be observed at the exposure time of ~90 min. The difference in the fluorescence is also seen in fluorescence measurements in FIG. 9c and confirms this analysis.

To demonstrate utilizing the multiplex system as a TTI by defining a set temperature, the exposure was estimated at the three locations indicated by the circles in FIG. 13A. Three temperature response curves were selected and the estimated time at those temperatures was found for each location (see Table 2). It should be noted that the temperatures selected were chosen specifically to be close to the temperature measurements of the thermocouples at each of the locations to demonstrate the accuracy of the system. The bold value represents the estimated exposure time for the response curve closest to the measured temperature at that location.

TABLE 2

Estimated exposure times using set temperature method.

| Loc. | $I_{540}/I_{560}$ | F value | $t_{232.2}$ (min) | $t_{221.1}$ (min) | $t_{210}$ (min) | TC measurement |
|---|---|---|---|---|---|---|
| 1 | 1.084 | 6.37 | 87.6 | 173 | 359.1 | ~90 min @ 231.1° C. |
| 2 | 1.009 | 1.802 | 41.9 | 83.6 | 156.7 | ~89 min @ 222.8° C. |
| 3 | .994 | 0.823 | 24.4 | 49.7 | 85.6 | ~86 min @ 208.9° C. |

The most interesting feature in Table 2 comes when comparing the estimated times for the temperature response curve closest to the thermocouple measurement at that location. For all the locations the best time estimate is within 6 minutes of the actual measurement with relative errors less than or equal to 6%. This shows the multiplex system has great accuracy. From Table 2 it can also be seen that if the exposure temperature at a location is lower than the set temperature that the estimated time is less than the actual exposure time. Similarly the estimated time for a location that was exposed at a temperature higher than the actual temperature is greater than the actual time. Thus even though the defined temperature may not match the exposure temperature it is possible to get an idea of how much significant the thermal exposure to the part was.

3.3.2 Set Time

The set time method was applied to the same measurement as the set temperature method (FIG. 9). The temperatures estimated by using the measured F values and a set time of 90 min are shown in Table 3. This time was specifically chosen to match the experimental conditions to display the accuracy of the multiplex TTI.

TABLE 3

Estimated exposure temperatures using a set time of 147 min.

| Location | $I_{540}/I_{560}$ | F value | $T_{90}$ (° C.) | TC measurement |
|---|---|---|---|---|
| 1 | 1.084 | 6.37 | 231.7 | ~90 min @ 231.1° C. |
| 2 | 1.009 | 1.802 | 219.5 | ~89 min @ 222.8° C. |
| 3 | .994 | 0.823 | 209.1 | ~86 min @ 208.9° C. |

From Table 3, it can be seen that the estimated temperatures compare very favorably to the thermocouple measurements with the relative error being less than 2%. These results indicate the great potential that the multiplexed system of has as a TTI for characterizing thermal exposure in the range of ITD in CFRP.

4. Summary

The kinetics of fluorescent thermal damage probes AJNDE16 and AJNDE35 were characterized using fluorescence intensity measurements. Kinetic models for both probes were developed using exponentially modified Gaussian functions to represent the fluorescence emission of the probes. A multiplexed system combining both AJNDE16 and AJNDE35 in the same sample was demonstrated which showed that the spectra shifted as a function of time and temperature giving it the potential to be used as a TTI. It was found that the multiplexed system could be model as the superposition of the kinetic models of the individual probes. Using ratiometric fluorescence a response function for the multiplexed system was developed. The TTI capabilities of the multiplexed system using the response function were demonstrated using the multiplexed epoxy as a coating on composite panel that was locally heated. The response function could be utilized by setting a temperature and estimating the time or vice versa. Using these methods the accuracy of the system was shown to be excellent when the experimental conditions matched the set parameter with error less than 6%. Even when the exposure conditions did not match the set parameters, it was still possible to obtain an estimate of how significant the thermal exposure was.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of monitoring thermal exposure of a composite, comprising:
   (a) providing a composite, comprising:
      (i) a matrix;
      (ii) a first probe, wherein the first probe is not luminescent until activated by heat to a temperature above 200° C., after which it becomes luminescent and has a first luminescence profile; and
      (iii) a second probe, wherein the second probe is not luminescent until activated by heat, after which it becomes luminescent and has a second luminescence profile that is different from the first luminescence profile;
   (b) exposing the composite to a time-temperature profile that includes a portion of time at a temperature above 200° C.; and
   (c) measuring an optical property of the composite.

2. The method of claim 1, wherein the matrix is selected from the group consisting of a thermoset polymer, a thermoplastic polymer, and a sol-gel.

3. The method of claim 1, wherein the optical property is stimulated emission of the first probe.

4. The method of claim 1, wherein the first probe is fluorescent or phosphorescent.

5. The method of claim 1, wherein the matrix is transparent at wavelengths within the first luminescence profile.

6. The method of claim 1, wherein the first probe is incorporated within the matrix.

7. The method of claim 1, wherein a coating on the matrix comprises the first probe.

8. The method of claim 1, wherein the time-temperature profile comprises a rise in temperature from a first temperature to a second temperature between a first time and a second time.

9. The method of claim 8, wherein the time-temperature profile comprises temperature variations.

10. The method of claim 8, wherein the time-temperature profile comprises repeated temperature cycles.

11. The method of claim 1, wherein the first probe and the second probe combine to be a time-temperature indicator of thermal damage.

12. The method of claim 1, wherein the optical property is the combined stimulated emission of the first probe and the second probe.

13. The method of claim 1, further comprising a step of analyzing the optical property to determine thermal exposure of the composite.

14. The method of claim 13, wherein the step of analyzing the optical property comprises comparing the optical property to a calibration data set.

15. The method of claim 1, wherein the matrix further comprises carbon fibers.

16. The method of claim 15, wherein the matrix is a carbon-fiber reinforced plastic composite.

17. The method of claim 1, wherein the composite is a structural component of a vehicle.

18. The method of claim 17, wherein the composite is a structural component of an aircraft.

* * * * *